United States Patent
Le Page et al.

(10) Patent No.: US 6,221,648 B1
(45) Date of Patent: Apr. 24, 2001

(54) HETEROLOGOUS GENE EXPRESSION IN LACTOCOCCUS, AND THE EXPRESSION PRODUCTS THEREFROM

(75) Inventors: Richard William Falla Le Page; Jeremy Mark Wells; Peter William Wilson; Pamela Norton De Villareal, all of Cambridge (GB)

(73) Assignee: Microdial Technics Ltd., Cambridge (GB)

(*) Notice: Subject to any disclaimer, the term of this patent is extended or adjusted under 35 U.S.C. 154(b) by 0 days.

(21) Appl. No.: 08/290,995

(22) PCT Filed: Mar. 1, 1993

(86) PCT No.: PCT/GB93/00425

§ 371 Date: Oct. 27, 1994

§ 102(e) Date: Oct. 27, 1994

(87) PCT Pub. No.: WO93/17117

PCT Pub. Date: Sep. 2, 1993

(30) Foreign Application Priority Data

Feb. 27, 1992 (GB) .................................................. 9204237
Sep. 21, 1992 (GB) .................................................. 9219890

(51) Int. Cl.$^7$ ............................ C12N 15/74; C12N 15/09
(52) U.S. Cl. ........................ 435/252.3; 435/69.1; 435/471
(58) Field of Search ............................... 435/252.3, 69.1, 435/471; 514/2; 424/93.4, 93.44

(56) References Cited

U.S. PATENT DOCUMENTS

| 4,948,734 | 8/1990 | Edwards et al. | 514/2 |
| 4,952,496 | 8/1990 | Studier et al. | 435/91.41 |
| 5,126,251 | 6/1992 | Moss et al. | 435/69.1 |
| 5,135,855 | 8/1992 | Moss et al. | 435/69.1 |

FOREIGN PATENT DOCUMENTS

| 178863 | 4/1986 | (EP) . |
| 207459 | 1/1987 | (EP) . |
| 307011 | 3/1989 | (EP) . |
| WO8810307 | 12/1988 | (WO) . |
| WO9105866 | 5/1991 | (WO) . |

OTHER PUBLICATIONS

Mukhergee, A., "New Plasmid Constructions for High Level Production of Eukaryotic Proteins," *National Institutes of Health*, published specification to U. S. Patent Application No. 07/255,723 (1988).

Bojovic, B., et al., "Improved vector for promoter screening in lactococci," *Appl. Environ. Microbiol.* 57:385–388 (1991).

Sibakov, M., et al., "Secretion of TEM B–lactamase with signal sequences isolated from the chromosome of *Lactococcus lactis* subsp. *lactis*.", *Appl. Environ. Microbiol.* 57:341–348 (1991).

van de Guchte, M., et al., "Construction of a lactococcal Expression vector: expression of hen egg white lysozyme in *Lactococcus Lactis* subsp. *lactis*.", *Appl. Environ. Microbiol.* 55:224–228 (1989).

van de Guchte, M., et al., "Heterologous gene expression in *Lactococcus lactis* subsp. *lactis*. synthesis, secretion and processing of the *Bacillus subtilis* neutral protease", *Appl. Environ. Microbiol.* 56:2606–2611 (1990).

Pillidge, C. J., et al., "Expression of a B–galactosidase gene from *Clostridium acetobutylicum* in *Lactococcus lactis* subsp. *lactis*.", *J. Appl. Bacteriol.* 71:78–85 (1991).

Iwaki, M., et al., "Oral immunization with recombinant *Streptococcus lactis* carrying the *Streptococcus matuns* surface protein antigen gene.", *Infect. Immunity* 58:2929–2934 (1990).

Studier, F. W., et al., "Use of T7 RNA polymerase to direct expression of cloned genes", *Methods in Enzymology* 185:60–89 (1990).

de Vos, W. M., Gene cloning and expression in lactic streptococci,*FEMS Microbiol. Reviews* 46:281–295 (1987).

Hager, P. W., et al., "Translational specificity in *Bacillus subtilis*", In D.A. Dubnau (ed.), *The Molecular Biology of the Bacilli*, Academic Press, Inc., N.Y., II:1–29 (1985).

Klipper–B_Iz, et al., "Nucleic acid hybridization of group N and group D streptococci", *Curr. Microbiol.* 7:245–250 (1982).

de Vos, W. M., et al., "Structure and expression of the *Lactococcus lactis* gene for phospho–b–galactosidase (lacG) in *Escherichia coli* and *Llactis*", *J. Gen. Microbiol* . 135:1833–1846 (1989).

Feitelson, et al., "*Bacillus Thuringiensis:* Insects and Beyond", *Biotechnology* 10:271–275 (1992).

de Vos, W. M., "Gene Cloning in *lacti Streptococci*," *Neth. Milk Diary J.* 40:141–154 (1986).

Wells et al. "A model system for the investigation of heterologous protein secretion pathways in *Lactococcus lactis* ", *Appl. Environ. Micribiol.* 59: 3954–3959, Nov. 1993.*

Wells et al. "*Lactococcus lactis* : high–level expression of tetanus toxin fragment C and protection against lethal challenge", *Molec. Microbiol.* 8: 1155–1162, Jun. 1993.*

* cited by examiner

Primary Examiner—Scott D. Priebe
(74) Attorney, Agent, or Firm—Hale and Dorr LLP

(57) ABSTRACT

Heterologous polypeptides are produced in lactococcus using a T7 or T7-like RNA polymerase gene under the control of an inducible promoter effective in a lactococcus host, and a promoter specific for said polymerase upstream of a coding sequence for the heterologous polypeptide. Thus, the promoter specific for the polymerase directs transcription of the coding sequence selectively as a result of expression of the polymerase. The heterologous polypeptide can be produced at high yield, and can be secreted. The polypeptide within the cell, being biologically active, can be delivered in the encapsulated form, e.g. as a medicament, vaccine or as an environmental pesticide.

2 Claims, 17 Drawing Sheets

MCS = Multiple cloning site

Figure 1:
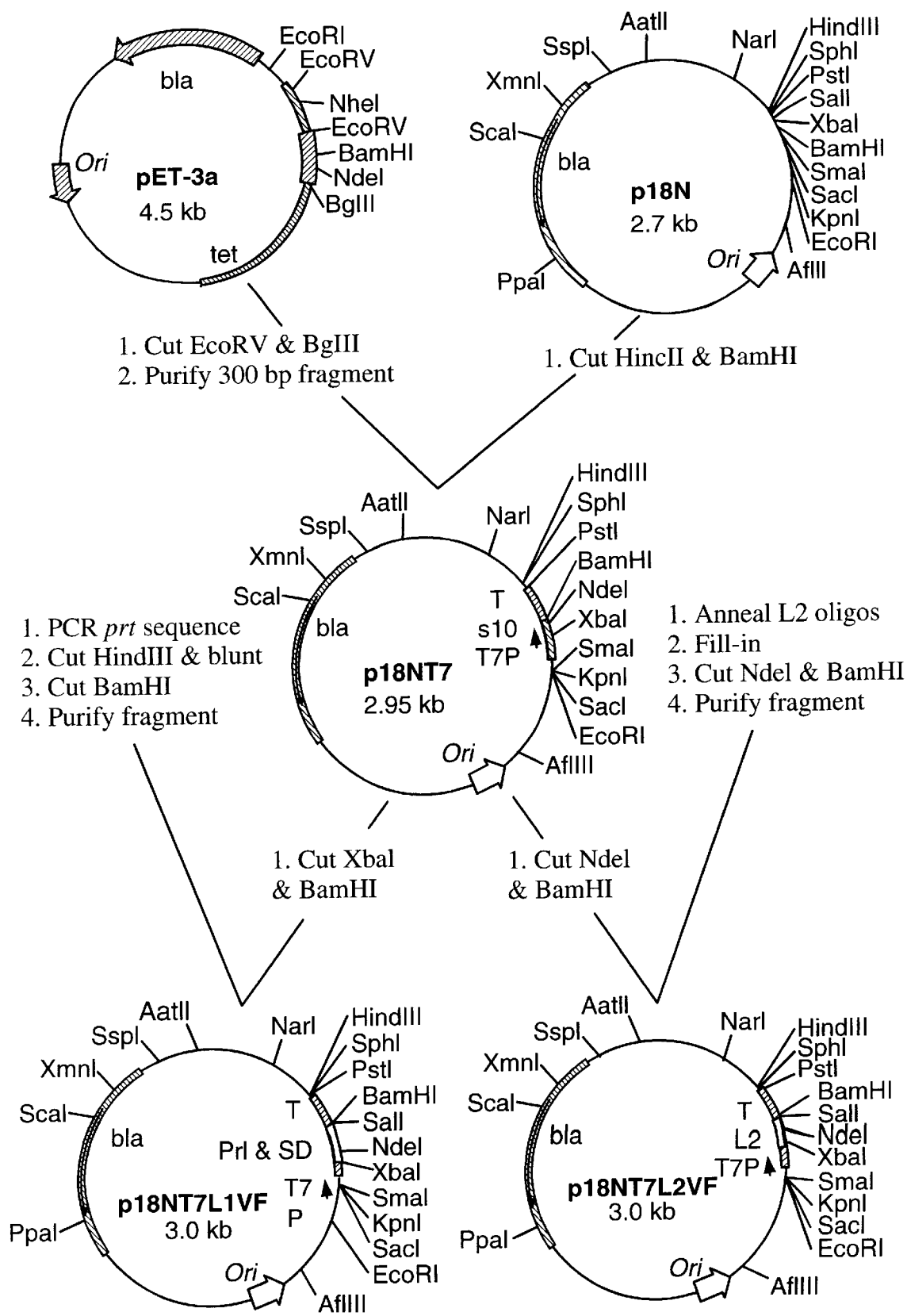

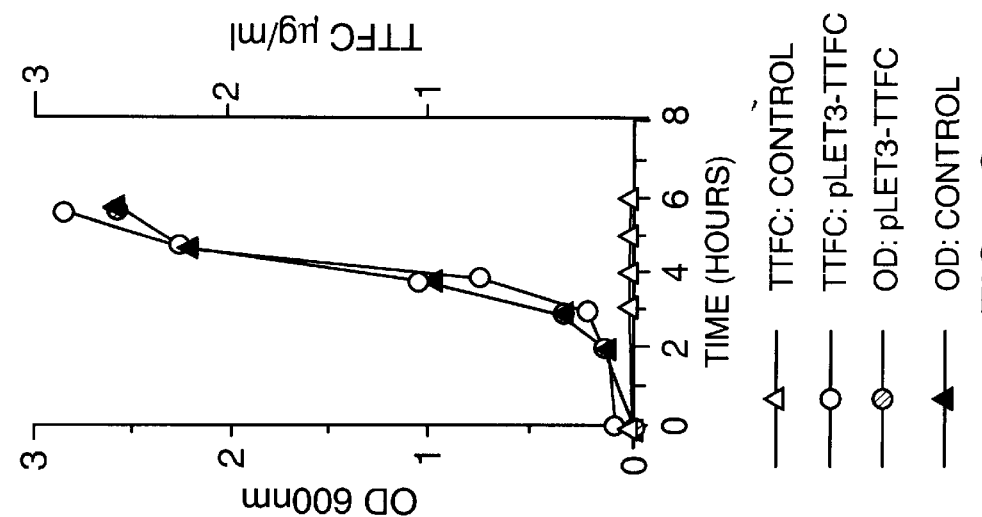
FIG. 8C
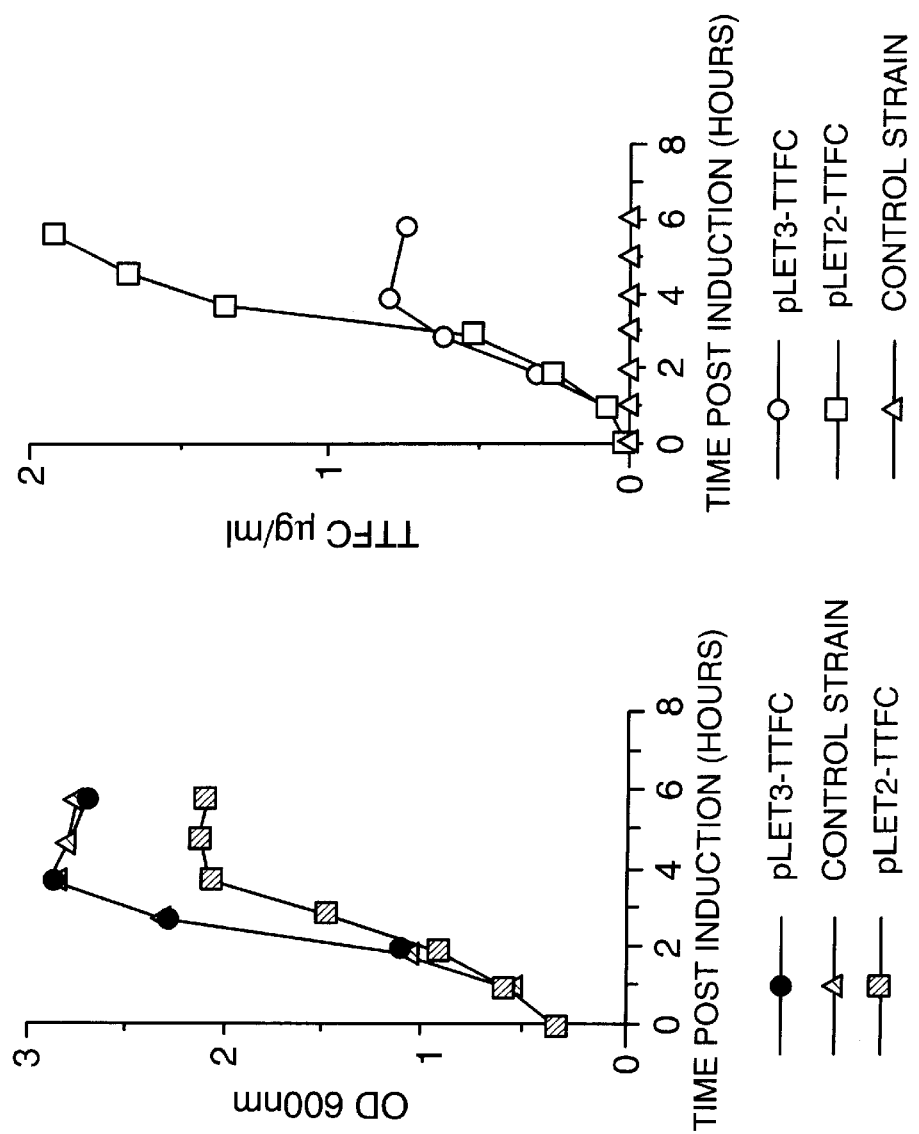
FIG. 8B
FIG. 8A key:

L2; signal secretion layer 2
T; terminator
TTFC; tetanus toxin fragment C
V3a; V3a fragment containing the V3 loop of HIV-MN
Ori; replicon
 ; T7 RNA polymerase specific promoter CryIA gene pWW-5' CryIA pWW-PCR CryIA pWW-CryIA p19NT7-CryIA

HETEROLOGOUS GENE EXPRESSION IN LACTOCOCCUS, AND THE EXPRESSION PRODUCTS THEREFROM

FIELD OF THE INVENTION

This invention relates to the expression of heterologous proteins in lactic acid bacteria, and to their use in producing an immune response in an immunised subject. The invention also provides certain specific expression products of considerable potential usefulness.

BACKGROUND OF THE INVENTION

Bacteria able to produce and secrete proteins encoded by heterologous genes are used extensively for the industrial production of high value-added pharmaceutical proteins such as human and animal growth hormones, insulin, interferons, cytokines etc. Organisms other than *E. coli* thus far used or proposed for industrial production include cultured mammalian and insect cells, yeasts and fungi, and a number of Bacillus spp. Among the bacteria already widely used for industrial purposes are the lactic acid bacteria, which are employed as starter cultures for fermented foodstuffs, and as flavour enhancers, and preservatives. These properties depend on the ability of these organisms to produce certain enzymes, lactic acid and harmless antimicrobial polypeptides such as nisin. To date only low yields of foreign proteins have been obtained by the genetic manipulation of these organisms, and in some instances gene expression has depended on the use of unregulated genes, or of undefined control elements. Lactic acid bacteria which are related to those used in food and milk fermentations are also found as commensal bacteria in the alimentary tracts of animals. There is considerable industrial interest in the genetic manipulation of both the food and the commensal bacteria. For example, recombinant strains of these bacteria could be used to improve fermentation processes, and as novel vectors for multi-disease vaccines.

In contrast to a Gram-negative organism such as *E. coli* Gram-positive bacteria such as the lactic acid bacteria and Bacillus spp. have the capacity to secrete proteins more readily into the growth medium. However, the active protease systems of the best known bacillus species, *B. subtilis*, have greatly limited the usefulness of this organism for the production of recombinant proteins. Protein secretion in Gram-positive cells differs fundamentally from that observed in Gram-negative cells, where it is a complex two stage process in which true secretion (as opposed to protein accumulation in the periplasmic space) requires that exported proteins should traverse both the cell membrane and the outer membrane. Thus, although large amounts of recombinant proteins can be produced in *E. coli* many of these proteins become insoluble and inactive, and either accumulate within the cytoplasm, or are secreted as far as the periplasm, where they may precipitate, and lose their biological activities. For many such recombinant proteins renaturation procedures for the recovery of biological activity are an expensive and difficult aspect of downstream processing. For these reasons the use of naturally secretory organisms for protein production may be highly advantageous.

As a separate aspect of the development of bacterial technologies, recombinant vaccine strains of certain pathogenic bacteria (mycobacteria, salmonella) have been proposed for the production and delivery in vivo of protective protein antigens of a range of disease-causing bacteria, viruses, and protozoan and metazoan parasites. However, even attenuated vaccine strains of pathogenic bacteria are to some degree invasive, and the immune responses generated by these organisms may result in immunopathological damage. Development of non-invasive microbes in forms suitable for effective antigen-presentation to the immune system would provide previously unattainable levels of vaccine safety. In particular, if given by the oral route, such organisms might stimulate the mucosal immune system preferentially, thus providing a basis for the development of live, oral vaccines which would protect against infection. Alternatively or additionally these vaccines might be given by injection, or administered orally or by injection to boost immune responses primed with recombinant mycobacteria or salmonella; in this instance the innate differences between the antigenic constituents of the priming vaccine carrier and those of the booster could be expected to minimise immunopathological damage, and to boost immune responses to the expressed recombinant antigens preferentially. Furthermore, the capacity to express a range of foreign proteins in non-invasive microorganisms opens the way to the concurrent delivery of antigens and cytokines, which might be used to drive an immune response in a desired direction. The successful development of all these applications requires that a regulated system for high level foreign gene expression should be available for use in lactic acid bacteria.

Although there are several reports of the expression of foreign genes in *L. lactis* none of these describes either a regulated system, or the production of substantial quantities of protein. In two of these cases antibiotic resistance genes were used as reporter genes to identify secretion signal sequences and/or promoter sequences[1,2]. The other five cases comprise two proteins of eukaryotic origin and three prokaryotic proteins of Gram-positive origin. The eukaryotic proteins concerned are hen egg white lysozyme and bovine prochymosin. The prokaryotic proteins are *Bacillus subtilis* neutral protease, the β-galactosidase of *Clostridium acetobutyicum* and the pAC protein antigen of *Streptococcus mutans*. The results obtained with these latter three proteins provide the best comparison with our own work, since we have also used as a model system one which involves the expression of a protein of Gram-positive origin (the tetanus toxin fragment C). However, our own results are unique, in that we have devised a system of regulated gene expression and product secretion, and also obtained significant yields of the expressed protein product, whether secreted or not. The previous studies have resulted in only low and (with one exception) undetermined amounts of foreign protein being formed, whereas the system we have developed has reliably yielded 3.4% of soluble cytoplasmic protein as the desired product with a secretory expression system, and 22% of soluble cytoplasmic protein with a non-secretory expression system. In addition, with the secretory system, product is secreted into the supernatant in a progressive fashion, reaching an estimated final yield (under test-tube conditions) of 5–10 mg/L.

In the studies cited above hen egg white lysozyme[3] was expressed as a fusion protein which either lacked activity or was produced in too low an amount to be detected in the assay used. Biologically active *Bacillus subtilis* neutral protease[4] was expressed and secreted from *L. lactis* using either its own promoter or a lactococcal promoter. The amounts of neutral protease produced (in arbitrary units) were reported to be only 1–2% of those produced by the same plasmid constructs in *Bacillus subtilis*[4]. The β-galactosidase from *Clostridium acetobutylicum*[5] was introduced into a lactococcal starter train, and enzyme activity detected. However, the maximum level of enzyme activity obtained was less than half of that measured in a wild type strain of L. lactis with innate β-galactosidase activity. In all these instances no details are given of actual amounts of expressed protein present in the transformants. Expression of the bovine prochymosin[6] gene in L. lactis has also been reported. Chymosin is an enzyme which is normally formed in the abomasum of young calves. It is a casein-specific protease used to curdle milk for cheese making. The gene encoding the precursor of chymosin (prochymosin) has been constitutively expressed in L. lactis using the promoter and secretion signal sequence of the proteinase gene of S. cremoris strain SK11; this work is the subject of European patent application number 88201203.2, filed on Jun. 13, 1988. The authors do not indicate the quantities of prochymosin produced in their expression strains of L. lactis but our inspection of the Western blots implies that the levels of expression obtained were low (estimated to be 0.2 mg/L supernatant). Only trace amounts of recombinant protein were detected in whole cell extracts.

Perhaps the best comparison with our own work is that which has been carried out on the pAC protein (a surface antigen) of Streptococcus mutans[7]. This was expressed in L. lactis by the introduction into L. lactis of a plasmid carrying the pAC gene within a 6.2 kb SphI-BamHl DNA fragment derived from S. mutans. No attempt was made to control the expression of the gene. The yield of pAC protein in L. lactis was approximately 0.2% of dry weight, as compared to 1% in S. mutans. The pAC protein is secreted into culture supernatants of S. mutans to a level of approximately 5.5 mg/L. Because the pAC protein as produced in L. lactis lacked its cell membrane anchor domain it was anticipated that it would be efficiently secreted. However, this did not occur, the final yield of pAC protein in the L. lactis supernatants approached the limits of detection.

SUMMARY OF THE INVENTION

One aspect of the present invention provides a method which permits the high level regulated expression of heterologous genes in L. lactis and the coupling of expression to secretion.

In the examples herein we use the same t7 bacteriophage RNA polymerase and its cognate promoter used to develop the most powerful E. coli expression system available[8]. The E. coli T7 system relies on the regulated expression of the fast RNA polymerase which then acts specifically on its cognate promoter to transcribe the target gene. The T7 RNA polymerase transcribes RNA approximately 4–5 times faster than the E. coli polymerase and under optimum conditions the entire resources of the cell can be devoted to the production of foreign protein. The T7 RNA polymerase is indeed so efficient that it is necessary to tightly regulate its expression in E. coli, especially if the target gene product is likely to be detrimental to the host. In E. coli the RNA polymerase gene expression is regulated by use of the lac promoter and can be induced by lactose or the gratuitous chemical inducer IPTG. However, it is often necessary to maintain these plasmids in host strains which produce T7 lysozyme. This enzyme is able to inhibit the activity of the T7 RNA polymerase produced by 'leaky' expression in the absence of the inducer.

It was not obvious that the T7 polymerase system would function in L. lactis with the efficiency we report since many difficulties are commonly encountered in achieving high level gene expression in new types of microorganisms. The expression signals identified in Lactococcus show an organisation which is characteristic for Gram-positive bacteria[9], suggesting that a heterospecific barrier to the expression of genes from Gram-negative organisms might be expected. Furthermore, rare codons in the genes of Gram-negative organisms[10] are commonly used in L. lactis. This arises from a relatively low G+C content[11] and a strong bias for A or T especially in the third position of lactococcal codons. It seems reasonable therefore to assume that the codon composition is under strong selective pressure and that a poor fit between the codon bias of Gram-negative and Gram-positive organisms would also limit the levels of heterospecific gene expression. A striking preference for the leucine CUU codon has been reported in L. lactis [12] and we have also noted a strong bias for the Gln codon CAA (51 of 52 codons) in the lactococcal genes we have examined.

However, despite these considerations we have found that it is possible to develop an effective and regulated gene expression system in L. lactis by (1) placing expression of the T7 polymerase gene under the control of an inducible promoter derived from L. lactis and (2) directing secretion of the product by means of different secretion signal sequences of lactococcal origin. A unique feature of one of our target vectors is that the DNA sequence promoting the initiation of protein translation has been modified in such a way that the expressed gene product is secreted co-translationally and is not detected in the cytoplasm. This has the advantage that heterologous gene products which might be toxic to the cell or which might be subject to degradation in the cytoplasm can be secreted directly into the growth medium.

The reference to "T7-like RNA polymerase" includes, but is not limited to, those contemplated for example in U.S. Pat. No. 4,952,496 (Studier et al.), which mentions RNA polymerases from other T7-like phages, such as the T3 RNA polymerase. The important characteristics of a T7-like RNA polymerase are that there should be a cognate promoter which is highly specific for the polymerase and which is transcribed at a high level in the presence of the specific polymerase; so that transcription is not substantially effected by other polymerases in the cell, and can be controlled by controlling the expression of the specific polymerase.

Another feature of our invention lies in the discovery that the heterologous expression product which is retained intracellularly is in a soluble and/or biologically active form, unlike the aggregated and insoluble form so often found for example in heterologous polypeptides expressed in E. coli. Thus, this aspect of the invention provides soluble and/or biologically active heterologous proteins intracellularly accumulated in L. lactis, whether expressed in conjunction with a secretory expression system or not. In the latter case, the product can accumulate to remarkably high levels while remaining soluble and/or biologically active. Thus this aspect of the invention provides a valuable addition to the repertoire of techniques and materials available for recombinant DNA expression of biologically active proteins at useful levels.

This leads to another aspect of the invention which provides a novel approach to raising an immune response in an immunised subject since the immunogenically active protein can be delivered within the protection of the host cell, and moreover a host cell which is non-invasive and non-pathogenic, indeed a food-grade organism, which opens up further possibilities for mucosal, especially oral, administration of vaccines. The immunogenically active protein thus expressed may be used in its own right to raise an immune response against one or more epitopes on the protein; or it may be used as an immunogenic carrier protein to which the important epitope-bearing polypeptide is fused. An example given below is the HIV V3 loop protein fragment fused to TTFC. In general, therefore, the Lactococcus cells containing and/or expressing the immunogenic protein can be administered parenterally (e.g. subcutaneously) or mucosally (e.g. orally, nasally or rectally), to produce a systemic or mucosal immune response.

Over the past thirty years commercial use of pesticidal formulations of non-recombinant *Bacillus thuringiensis* (B.t.) has been restricted to a narrow range of caterpillar pests. However, investigators have discovered B.t. toxin-producing strains with specificities for a number of other pests. These newly-discovered strains include some with activity against plant- and animal-parasitic nematodes (Edwards et al. (1990) and U.S. Pat. No. 4,948,734). Such strains provide the first indication that B.t. toxins exist in nature which could be used to kill a wide range of ecto- and endo-parasites whilst causing no harm to their hosts.

The concept of expressing B.t. toxins from recombinant DNA in bacteria is already established[13], but this uses Gram-negative *Pseudomonas fluorescens* as a host, which has been chemically treated to kill and stabilize the organism. The use of a GRAS, especially foodgrade, organism should provide a safer and more environmentally acceptable host cell to encapsulate the B.t. toxin.

The present invention therefore enables foodgrade bacteria to produce substantial quantities of a B.t. toxin in a form that can be safely administered to a human or animal or applied environmentally as a biopesticide. For example, recombinant *L. lactis* expressing nematode toxins could be used for the treatment of nematode infections of man and animals.

Thus, the present invention can provide a route to simpler fermentation and production technology for B.t. derived products for safer use in the environment, but may also be applied to the treatment of human and animal pests which can be controlled by the ingestion or topical application of harmless B.t. toxin-producing bacteria.

A further aspect of the efficient expression of B.t. toxins in Lactococcus according to the present invention lies in the potential of these evolutionarily diverse proteins to act as immunogenic carriers for an epitope of interest. Thus, a polypeptide representing the latter epitope could be expressed as a fusion to an immunogenically active B.t. toxin (in the same way that the HIV V3 loop was fused to TTFC).

The term "biologically active" as used herein in relation to the heterologous polypeptide expressed in the Lactococcal host cell denotes that the polypeptide is produced in an appropriate conformation for obtaining biological activity, rather than a misfolded, aggregated and insoluble form which requires special denaturation and renaturation measures to achieve an appropriate conformation to any substantial extent. The term therefore includes polypeptide precursors of biologically active proteins, which are not themselves biologically active, but which can be readily converted into their biolgically active forms. For example, B.t. toxins may be produced as precursors which when used are converted in vivo into their toxic form.

BRIEF DESCRIPTION OF THE DRAWINGS

FIG. 1. Construction of T7 expression cassettes for use in *L. lactis* and *E. coli*. The EcoRV/BglII fragment of pET-3a containing the elements for expression by T7 in *E. coli* was transferred to p18N. These elements were modified in p18NT7L1 to replace the bacteriophage gene 10 translation initiation sequence with one of lactococcal origin and to provide a secretion signal sequence (L1) to which gene fusions could be made. In p18NT7L2 the bacteriophage gene 10 protein sequences were replaced with a different lactococcal secretion signal sequence (L2). Further details are given in FIG. 2. bla: beta-lactamase gene; tet: tetracycline resistance gene; Orr. origins of replication; T7P: T7 promoter; s10: gene 10 protein translation initiation region; T: terminator; L2: signal leader 2; PrtL & SD: Signal leader & protein translation initiation region of Prt gene. Arrow heads indicated direction of transcription.

FIG. 2. Sequences of the T7 cassettes constructed for expression and secretion in *Lactococcus lactis*. (SEQ ID NOS: 1–10) The cognate promoter of the T7 RNA polymerase is underlined in bold. The predicted transcription start site and last nucleotide of the terminated transcript are indicated +1 and −1 respectively. The protein sequences (SEQ ID NOS: 3,7, and 10) (numbered and with three letter amino acid codes) are shown above the nucleotide sequence. The potential stem loop structures at the 5' and 3' ends of the RNA are shown and the Shine-Dalgarno (SD) sequence in each construct is boxed. The signal peptide cleavage site is indicated by an arrow. The SalI fusion cloning site and other relevant sites are underlined. Parallel lines indicate that the sequence is not continuous. As indicated the T7, T7L1 and T7L2 cassettes have been incorporated into pLET1, pLET2 and pLET3 respectively.

FIG. 3. (A)*L. lactis*/*E. coli* shuttle vectors pMIG1 and pMIG3. (B) Two examples of the pLET plasmids for Lactococcal Expression by T7 RNA polymerase. pLET3 and pLET32 were derived from pMIG1 and pMIG3 respectively, containing respectively the L1 and L2 signal leader sequence (see FIG. 2 for details). (C) Plasmid pLET2-TTFC for expression of TTFC. Similar TTFC expression constructs were prepared using the other pLET vectors. kan: kanamycin resistance gene; cat: chloramphenicol acetyltransferase gene; Orr. origin of replication; T: terminator. Arrow heads indicate direction of transcription.

FIG. 4. Construction of a lactococcal vector for inducible expression of T7 RNA polymerase. bla: beta-lactzunase gene; Ori origin of replication; MLS: resistance to macrolides, lincosamides and streptogramin B-type antibiotics. Arrow heads indicate direction of transcription.

FIG. 5 (panel A). Coomassie stained gel of total cell protein extracts from strain pLET1-TTFC (track 1; TTFC arrowed) and the control strain (expression host strain harbouring pMIG1; track 2). Immunoblots of total cell extracts and supernatant proteins from the lactococcal expression strain harbouring pLET1-TTFC (panel B), pLET3-TTFC (panel C) and pLET2-TTFC (panel D) are shown. Approximately equal amounts of total cell protein from uninduced (U) and induced (i) cells or the protein precipitated from 200 $\mu$l of culture supernatant were loaded in each track. Total cell extracts or supernatant proteins from the pMIG1 control strain were loaded in tracks labelled TTFC; 2 $\mu$g in panel A; 500 ng in panels B–D). The sizes of the pre-stained marker proteins are indicated at the right. The unprocessed (u) and processed (p) forms of TTFC present in cell extracts of strain pLET2–17FC are indicated by arrows (panel D).

FIG. 6. Immunoblots of total cell extracts and supernatant proteins from the TTFC producing strains of *L. lactis* harbouring (A) pLET2-TTFC and (B) pLET32-TTFC. Approximately equal amounts of protein in the total cell extracts from uninduced (U) and induced (i) cells were loaded in each track. Total cell extracts or supernatant proteins from the host strain harbouring pMIG1 or pMIG3 were used as controls and loaded in tracks labelled C. Purified recombinant TTFC from *E. coli* (120 ng) was loaded into tracks labelled TTFC. The sizes of the pre-stained marker proteins loaded in tracks labelled M are indicated at the right. The unprocessed (u) and processed (p) forms of TTFC are indicated by arrows.

Figure 7A:
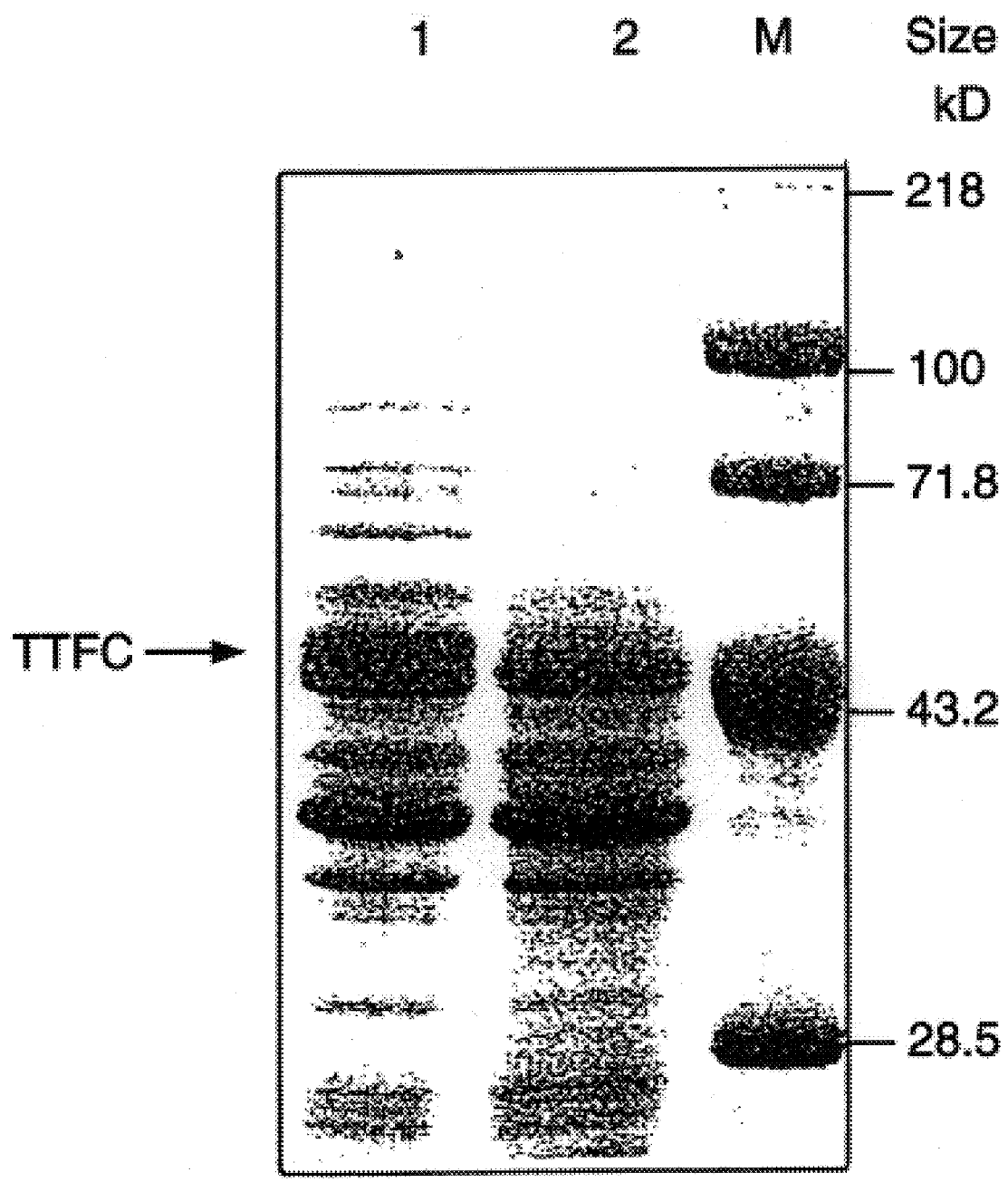
Figure 7B:
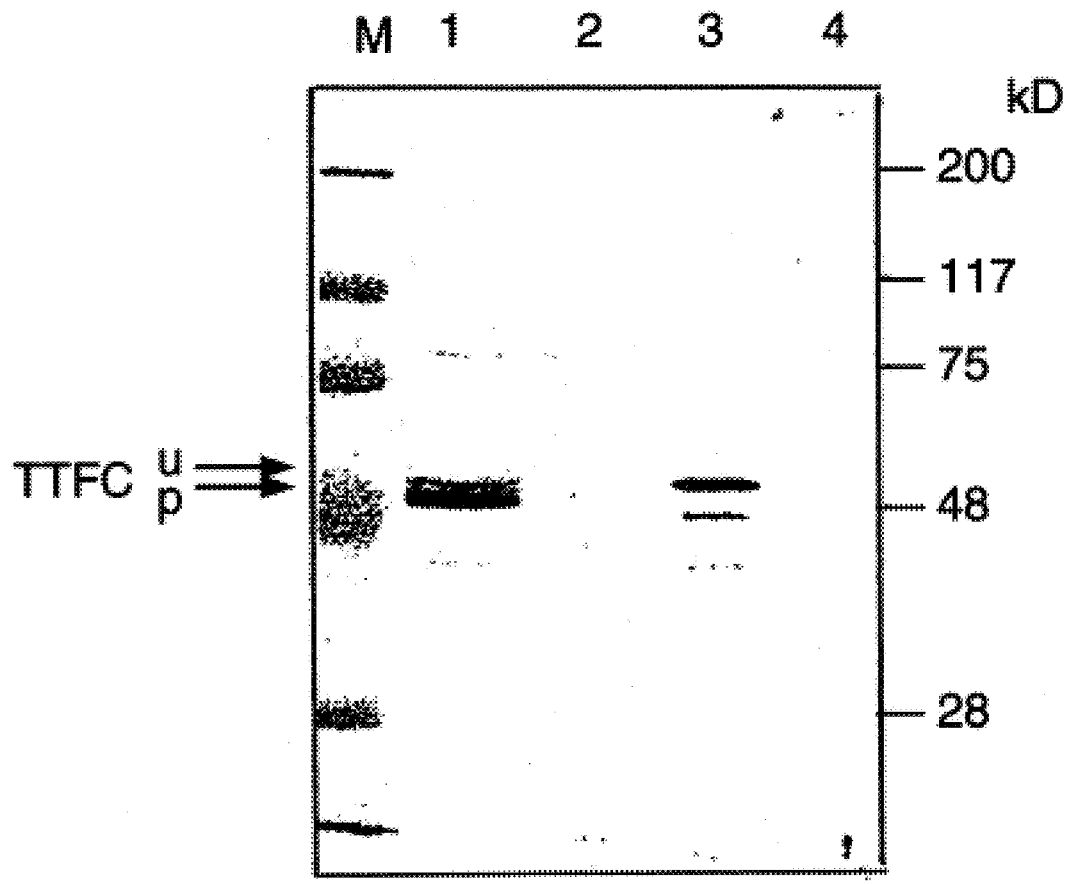

FIG. 7 (A). Coomassie blue stained protein gel of soluble protein extracts from expression strains of *L. lactis* harbouring pLET2-TTFC (track 1) or the vector control pMIG1 (track 2). M; marker protein track. The sizes of the pre-stained marker proteins are indicated at the right. The unprocessed (u) and processed (p) forms of TTFC are indicated by arrows.

FIG. 7 (B). Immunoblot of relative amounts of soluble and insoluble extracts from the *L. lactis* expression strain harbouring pLET2-TTFC or the vector control pMIG1. Tracks 1 and 3: pLET2-TTFC; soluble and insoluble extracts respectively. Tracks 2 and 4: pMIG1; soluble and insoluble extracts respectively. M; marker protein track. The sizes of the pre-stained marker proteins are indicated at the right. The unprocessed (u) and processed (p) forms of TTFC are indicated by arrows.

FIG. 8. (A). Growth curve of different strains after induction of TTFC expression in exponential phase of growth and (B) a graph showing amounts of TTFC secreted into the culture supernatant by these strains. (C) Graph showing the growth curve and amounts of TTFC secreted into the culture supernatant by the pLET3-TTFC and pMIG1 control strains when grown from low cell density in the presence of the lactose.

Figure 9:
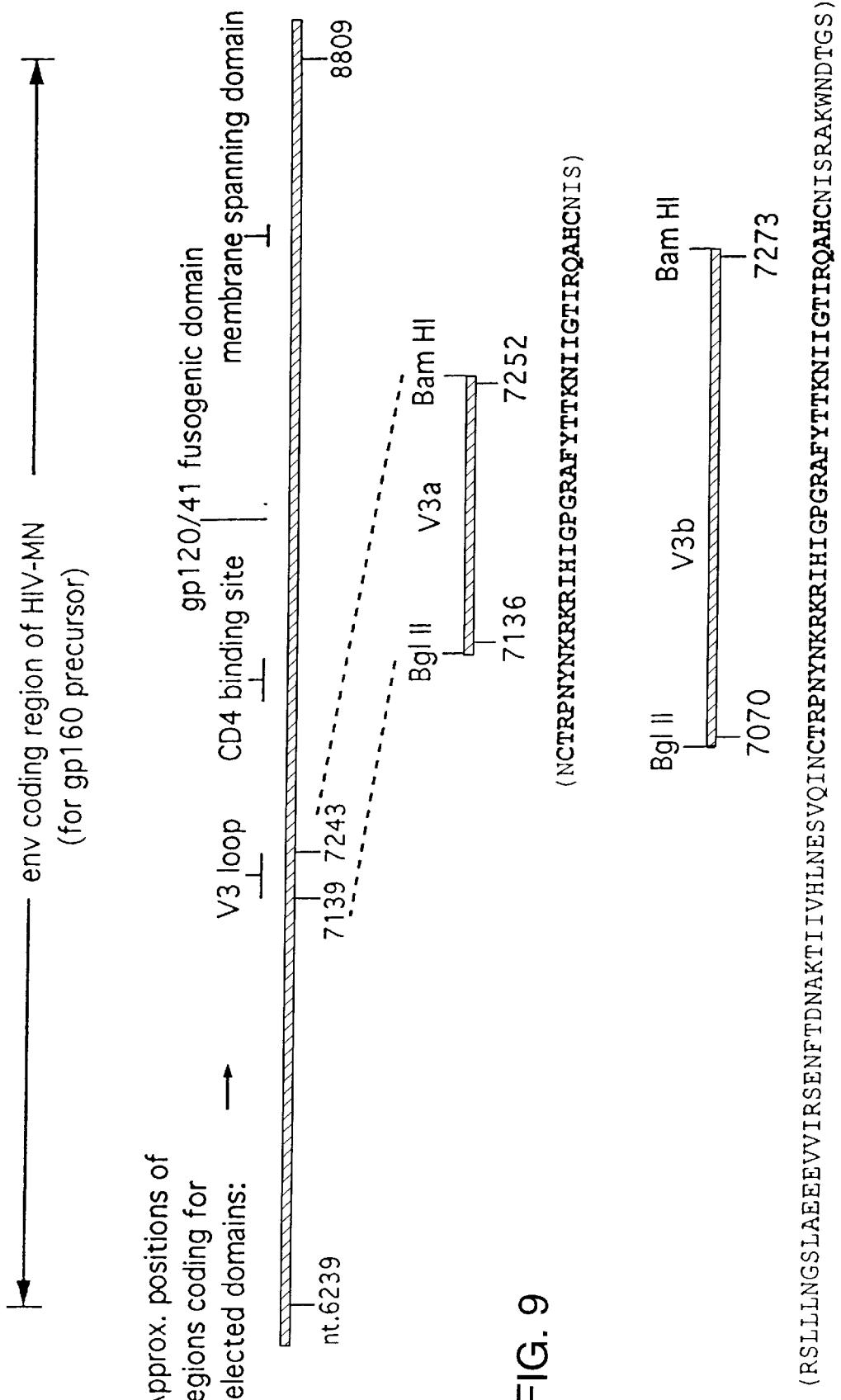

FIG. 9. Diagrammatic summary of the predicted positions of the PCR products V3a and V3b in relation to the HIV-MN proviral genome. The restriction enzyme sites shown at the ends of the products are those incorporated through the design of the primer oligonucleotides. The peptides (SEQ ID NOS: 11–12) coded for are shown in parentheses (V3 loop highlighted). The nucleotide numbering is that used in 'Human Retroviruses and AIDS 1989—a compilation and analysis of nucleic acid and amino acid sequences'.

Figure 10:
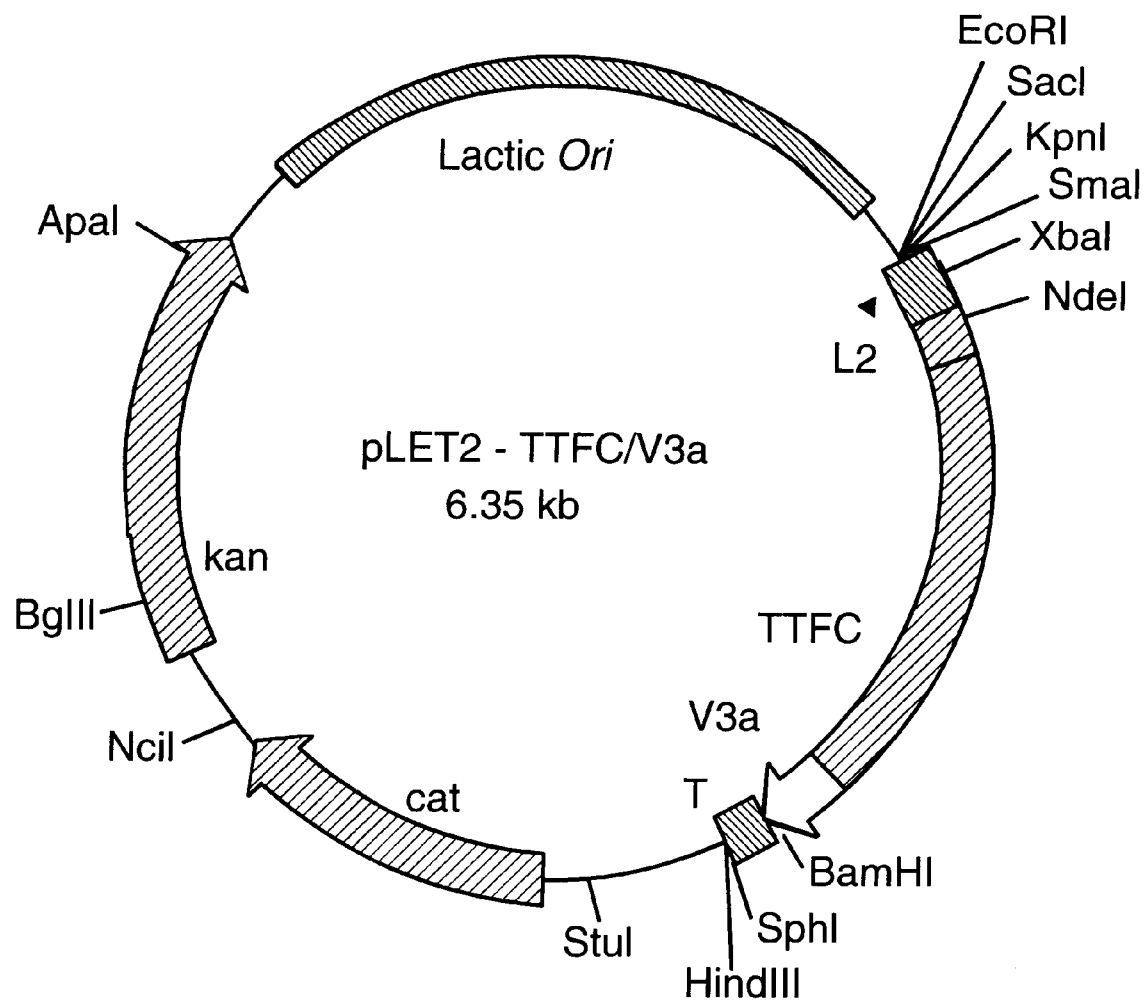

FIG. 10. Schematic representation of the plasmid pLET2-TTFC/V3a, for expression of the TTFC/V3a fusion protein in *L. lactis.*

Figure 11:
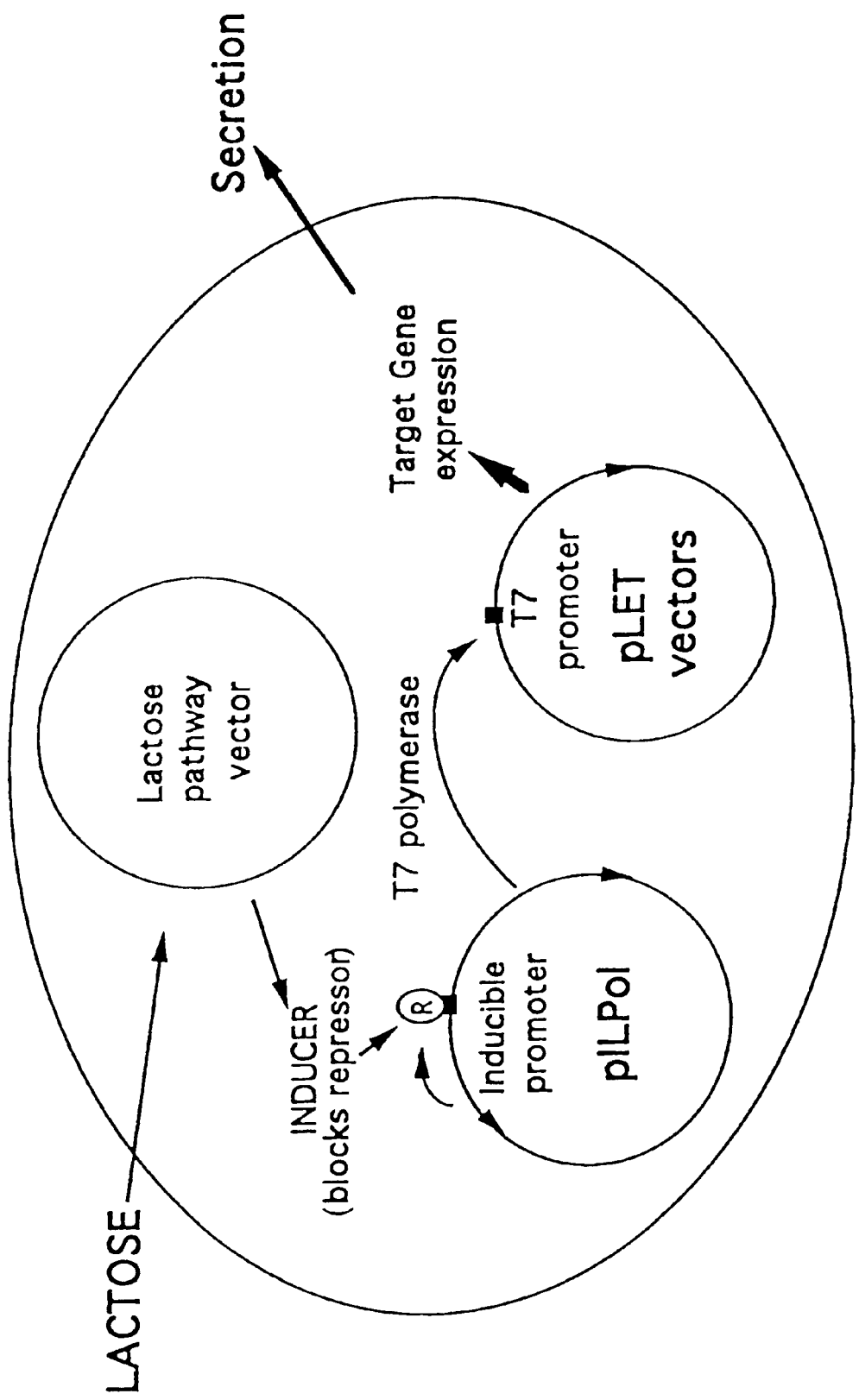

FIG. 11. Overview of the lactococcal expression system.

Figure 12A:
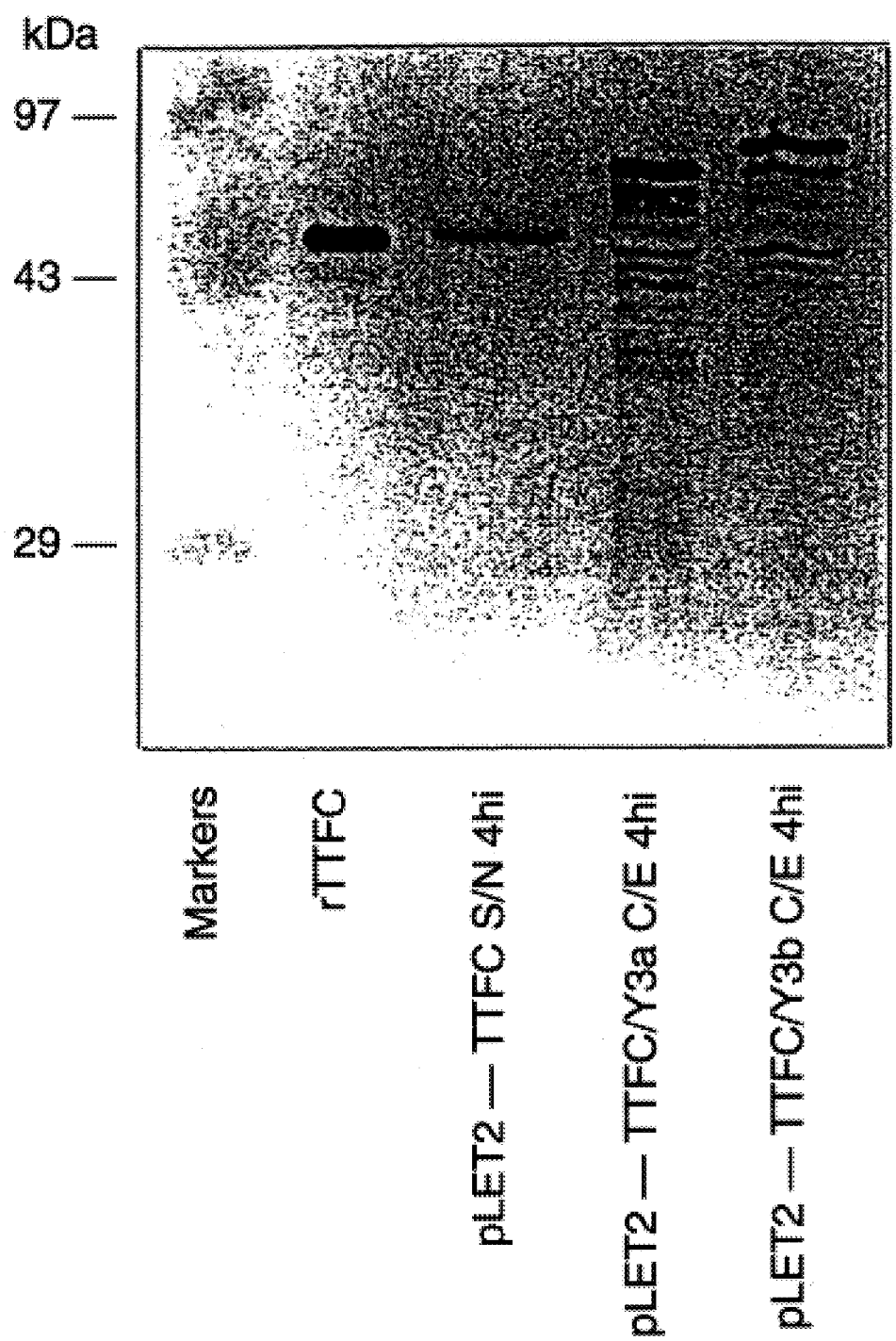
Figure 12B:
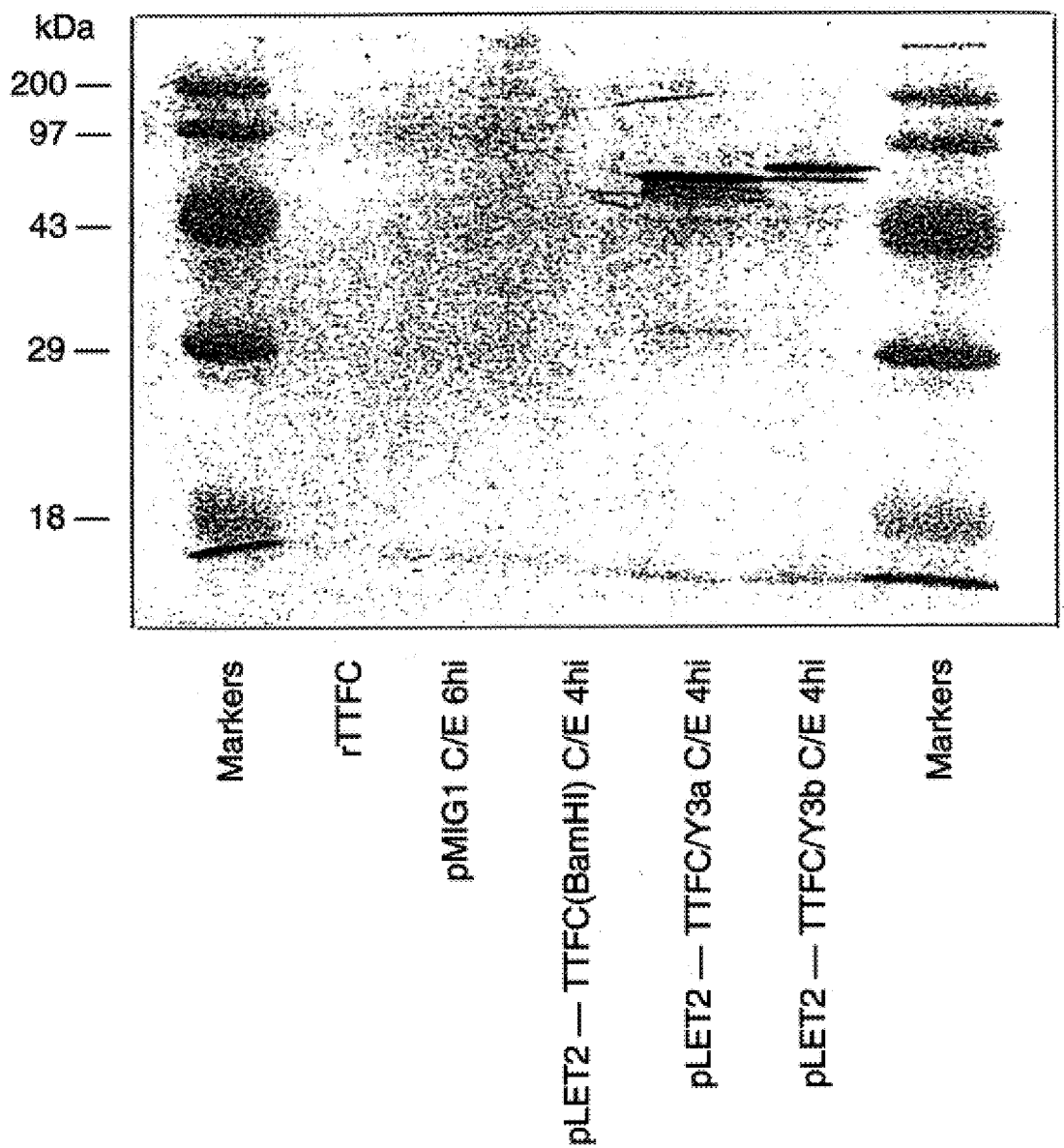
Figure 13A:
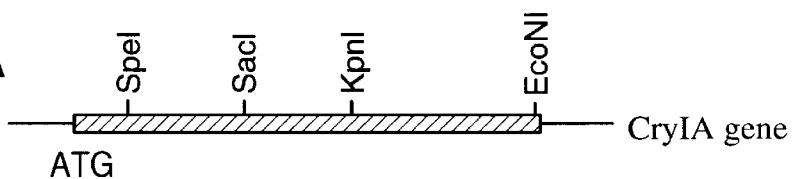
Figure 13B:
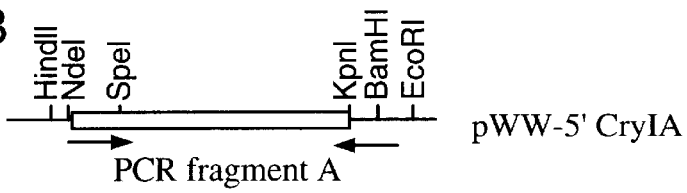
Figure 13C:
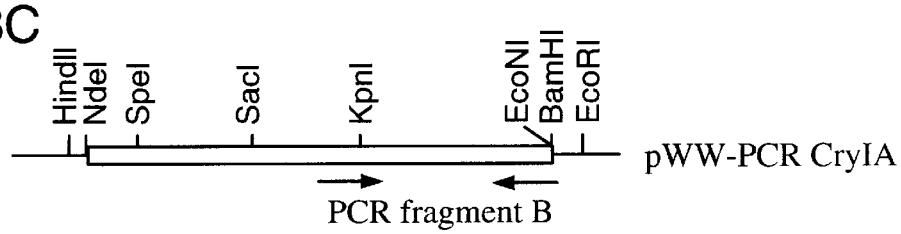
Figure 13D:
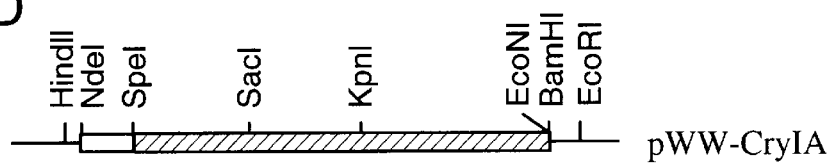
Figure 13E:
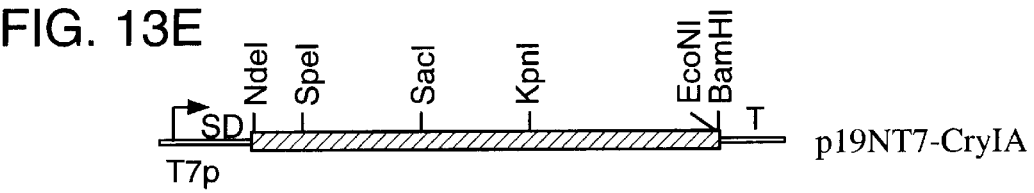
Figure 13F:
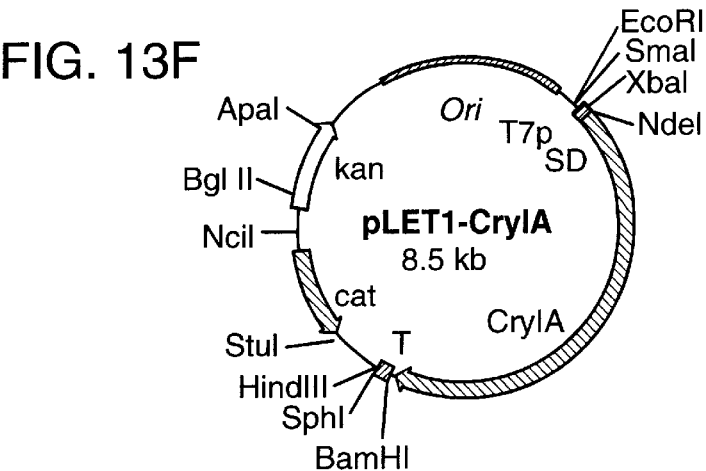

FIGS. 12A and 12B. Results from immunoblotting of *L. lactis* protein extracts using antibodies specific to TTFC and to the V3 loop of $HIV_{MN}$. 1820(plLpol) clones transformed by the plasmids denoted were grown in lactose containing media to induce expression of the foreign protein. At various times after induction whole cell and supernatant extracts were made from the cultures. Proteins were separated by SDS-polyacrylamide gel electrophoresis, blotted onto nitrocellulose and probed with:

a) a polyclonal rabbit antiserum raised against recombinant TTFC.

b) a human monoclonal antibody specific to the V3 loop of $HIV_{MN}$.

12a) Extracts probed with anti-TTFC polyclonal serum. Key:

rTTFC: recombinant TTFC (with no signal leader).

pMIG1: 1820(piLPol) clone containing the plasmid pMIG1 (pLET1 with no T7 RNA polymerase specific promoter).

pLET1 . . . : 1820(plLPol) clones containing the denoted plasmids.

C/E: cell extracts

S/N: supernatant extracts hi: hours after bacteria were resuspended in lactose containing media to induce expression of the foreign protein.

FIG. 13. Construction of the CrylA expression plasmid. (a) The CrylA gene and its relevant restriction endonuclease sites are shown in schematic form. (b and c) PCR derived fragments of this gene were assembled into the pUC derived general cloning vector pWW; the arrows indicate the position of the PCR primers with respect to the CrylA gene sequence. (d) The PCR derived CrylA gene fragment between the Spel and EcoNl sites in pWW-PCR CrylA was replaced with an identical fragment isolated from cloned *Bacillus thuringiensis* DNA (e) The Ndel—BamHl CrylA gene fragment was cloned into the 17 cassette in p19NT7. (f) The CrylA expression cassette was transferred into the pMIG1 shuttle vector to generate pLET1-CrylA. The coding sequences of the CrylA gene, chloramphenicol (cat) and kanamycin (kan) resistance genes are depicted as arrows on which the direction of transcription is indicated. Orr. origins of replication; T: terminator; T7p: T7 promoter.

FIG. 14. FIG. 2 (panel A). Coomassie stained gel of total cell protein extracts from the expression strain pLET1-CrylA (panel B) Immunoblot of a gel loaded as above using antisera to the crystal protein. Approximately equal amounts of total cell protein from uninduced (U) cells and induced cells at 30, 60 and 120 min after induction were loaded as indicated. 1 μg of purified crystal protein was loaded in tracks labelled CP. Extracts from the pMIG1 control strain harvested 120 min after induction were loaded in tracks labeled C. (panel C) The results of immunoblotting with subcellular fractions of the CrylA expressing cells. Proportional amounts of the total extract (TE), insoluble cell wall (W), membrane (M) and soluble protein (S) fractions were loaded as indicated. Purified crystal protein (1 μg) was run in the track labelled CP. In each panel the mobilitiy of the crystal protein is arrowed.

FIG. 15. (panel A) Immunoblot of total cell extracts from the pLET4-TTFC expressing strain and the control strain (C) 2 hours after induction. (panel B) The results of immunoblotting with subcellular fractions of the expressing cells. Proportional amounts of the insoluble cell wall (W), membrane (M) and soluble protein (S) fractions were loaded as indicated. The TTFC fusion protein detected using TTFC antisera is arrowed.

EXAMPLES

The following examples are given by way of illustration only, and are not to be taken as limiting the invention.

Example 1

1. Bacterial strains, plasmids and media.

The bacterial strains and plasmids used in this study are shown in Table 1. *L. lactis* was cultured in M17 broth or on M17 agar plates (Difco Ltd., London, UK) containing either 0.5% w/v glucose (GM17) or 0.5% w/v lactose (LM17). *E. coli* strains were grown in LB broth or on LB agar plates. *E. coli* strain 'SURE' was used as the host for the pUC based vectors because it over-produces the *E. coli* lac repressor protein. The *E. coli* RecA⁺strain MC1022 was used as the host for the pMIG1 shuttle vector and its derivatives and strain DH5a as a host for the pMIG3 shuttle vector and its derivatives. Erythromycin was used at a final concentration of 5 µg/ml for *L. lactis*. Chloramphenicol was added to *L. lactis* and *E. coli* cultures and plates to final concentrations of 5 µg/ml and 15 µg/ml respectively. Ampicillin was used at a concentration of 100 µg/ml.

TABLE 1

Bacterial strains and plasmids

| Bacterial Strain | Relevant properties. | Reference or source |
| --- | --- | --- |
| *L. lactis* | | |
| MG1363 | Plasmid free, Prt⁻ | 14 |
| MG1820 | MG1363 carrying the 23.5 kb lactose utilisation plasmid 1820, Prt⁻. | 15 |
| MG1820 (pILPol) | MG1820 carrying plasmid pILPol; host strain for lactose induced expression by T7 RNA polymerase. | This work. |
| *E. coli.* | | |
| SURE ™ | | 16 |
| MC1022 | | M. Gasson |
| DH5a | | 17 |
| pMIG1 | Camʳ *E. Coli/L. lactis* shuttle vector (for RecA⁺ *E. Coli*) High copy number in *L. lactis*. | Laboratory collection |
| pMIG3 | Camʳ *E. coli/L. lactis* shuttle vector. Several copies per cell in *L. lactis*; stable in RecA⁻ *E. coli* hosts. | Laboratory collection |
| pET-3a | Ampʳ, vector for expression by T7 RNA polymerase in appropriate *E. coli* host strains. | 8 |
| p18N | pUC18 with its single NdeI site inactivated by cutting with NdeI, blunt ending and religating. | This work |
| p18NT7 | Ampʳ, contains T7 sequences of pET-3a. | This work |
| p18NT7L1VF | Ampʳ, contains T7 elements and *L. lactis* prt gene SD & signal leader. | This work |
| p18NT7L2VF | Ampʳ, contains T7 elements and *L. lactis* usp 45 gene signal leader | This work |
| pAR1173 | Ampʳ, contains promoterless T7 RNA pol gene. | 18 |
| pUCPol | Ampʳ, contains promoterless T7 RNA polymerase gene on a BamHI fragment. | This work |
| pUCLacPol | Ampʳ, contains the *L. lactis* lac repressor gene and the T7 RNA pol gene under control of the *L. lactis* regulated lac promoter. | This work |
| pIL277 | Emʳ, low copy vector for *L. lactis* | 19 |
| pILPol | Emʳ, pIL277 containing the *L. lactis* lac repressor gene and the T7 RNA pol gene under control of the *L. lactis* regulated lac promoter. | This work |
| pSS1261 | *E. coli* expression vector pTTQ8 containing TTFC sequence. | 20 |
| pLET3 & pLET2 | Camʳ, pMIG1 based shuttle vectors for expression and secretion by T7 RNA polymerase | This work |
| pLET33 & pLET32 | Camʳ, pMIG3 based shuttle vectors for expression and secretion by T7 RNA polymerase | This work |
| pLET?-TTFC vectors | Camʳ, shuttle vectors for expression of TTFC in *L. lactis* by T7 RNA polymerase | This work |

2. DNA isolation and manipulation.

Large scale preparations of plasmid DNA were isolated from *L. lactis* by a modification of the Triton lysis method[21]. Mini-preparations of plasmid DNA from *L. lactis* were prepared by the Bimboim and Doly procedure[22] except that the cells were first incubated in 100 ml of TE (10 mM Tris-HCl, 1 mM EDTA, pH 8.0) containing freshly added lysozyme and mutanolysin to final concentrations of 5 µg/ml and 100 units/ml respectively. Also, the plasmid DNA recovered was treated with RNAase (100 mg/ml of DNAase free enzyme; 10 min at 37° C.) then proteinase K (200 µg/ml; 30 min at 37° C.), and finally extracted with phenol/chloroform mixture. The DNA was then precipitated and resuspended in TE. Plasmid DNA was isolated from *E. coli* as previously described and mini-preparations of plasmid DNA prepared by the alkali lysis method of Birnboim and Doly[22].

DNA was digested with restriction endonucleases under standard conditions and in the buffers recommended by the manufacturer. Other DNA modifying enzymes such as calf intestinal phosphatase, T4 DNA polymerase and T4 DNA ligase were used according to the recommendations of the supplier. General molecular cloning techniques and the electrophoresis of DNA in agarose gels were carried out essentially as described by Maniatis et al.[23] DNA fragments were purified from agarose gels by a spin column procedure which used a 0.5 ml microfuge tube plugged with a column of glass wool and punctured at the bottom with a fine needle. The slice of agarose gel containing the DNA fragment was placed on top of the glass wool and the whole tube placed in the top of a 2 ml microfuge tube. After 15 min centrifugation at full speed in a microcentrifuge the buffer and DNA from the gel slice was recovered from the bottom of the tube. The DNA was precipitated and used directly in ligations.

3. PCR.

PCR amplification of DNA was performed using high fidelity reaction conditions[24] and a thermal cycler (Cambio Ltd, Cambridge, UK). The reaction mixture contained 1×PCR buffer (10 mM Tris-Cl; pH 7.5 @ 70° C., 50 mM KCl), 250 µM of each deoxynucleoside triphosphate, 0.5 µM each primer, 1 mM $MgCl_2$, DNA template (typically 50–100 ng) and 2.5 units of Taq DNA polymerase (Cambio Ltd) in a total volume of 100 µl. The template DNA was heated for 5 min at 95° C. before adding the enzyme and then 30 cycles of PCR amplification run under the following conditions: denaturation at 93° C. for 1 min, primer annealing at 45° C. for 1 min, and extension at 72° C. for 1 min, with a final extension at 72° C. for 5 min. Synthetic oligonucleotide primers were designed to amplify the prt gene protein translation initiation sequences and its signal leader, based on the reported sequence[25].

Primer L1-sense (SEQ ID NO:13):
5'GATCGGCCAAGCTTCATATGAAACTTTTGGAAAGTGGAGGATATTGGA 3'

Primer L1-antisense: (SEQ ID NO:14):
5'CCGACGGATCCGTCGACCGCCGCCTTTGCTTGGATTTCGCCGACTGGC 3'

For amplification of the lactococcus lac promoter and lacR gene the same conditions were used. The primer sequences were as follows:

```
Primer 1:
(SEQ ID NO:15) CGGGATCCCGACAAACCATACATTAGAA

Primer 2:
(SEQ ID NO:16) CGGGATCCGAAATGCTACGTAGAAGTAC
```

In all cases the sequences underlined were identical with their templates.

4. Transformation.

*L. lactis* was transformed by electroporation of cells grown in the presence of glycine to weaken the cell wall. Several different parameters were investigated in order to optimise the procedure as follows; an overnight culture grown from a single colony was diluted about 100 fold in GM17 containing 3.0% glycine and grown to an $OD_{600nm}$ of 0.5–0.6 (this might take about 6 h). The culture was chilled on ice for 10 min and the cells pelleted by centrifugation (3000 G for 10 min) and resuspended in 0.2 vol of ice cold 0.5 M sucrose containing 10% glycerol. This washing step was repeated once more and 40 μl aliquots of the cells frozen in liquid nitrogen and stored at −70° C. Immediately before electroporation the cells were thawed on ice and 1–2 μl of the DNA solution (10–100 ng in de-ionised water) added. The cells were then transferred to ice cold electroporation cells (0.2 cm gap) and electroporated at 12.5 KV/cm, 400 Ohms resistance and 25 μF capacitance. Immediately after electroporation 960 μl of ice cold SGM17MC medium (GM17 plus 0.5 M sucrose, 20 mM $MgCl_2$ & 2 mM $CaCl_2$) was added to the cuvette and the cells transferred to a microcentrifuge tube on ice for 10 min. The cells were then incubated for 2 h at 30° C. in GM17 to allow the cells to recover before plating on GM17 antibiotic medium. Transformation efficiencies obtained using 10 ng of supercoiled plasmid DNA were typically in the order of $10^6$ colonies/μg of DNA following an overnight incubation at 30° C. *E. coli* were transformed by electroporation using standard procedures.[26]

5. Induction and analysis of target gene products.

The host lactococcal strains containing the target gene vectors were routinely grown in GM17 containing the selective antibiotic. Exponentially growing cells were induced by replacing GM17 for LM17. For the expression of target DNA the cells were grown at 37° C.

Total cell protein extracts were prepared from samples of approximately $1×10^9$ cells. The cells were harvested by centrifugation and resuspended in 100 μl of TE (10 mM Tris-HCl, 1 mM EDTA, pH 8.0) containing freshly added lysozyme and mutanolysin to final concentrations of 5 mg/ml and 100 units/ml respectively and incubated for 5–10 min at 37° C. The cells were then washed twice with 0.5 ml of TE and resuspended in 75 μl of TE. The cells were lysed following the addition of 2×SDS PAGE sample buffer[27] and boiled for 10 min to denature and solubilise the proteins.

TTFC was assayed from the supernatants of cultured bacteria using ELISA and Immunoblotting techniques. After the cells were pelleted by centrifugation 5 ml aliquots of the supernatant were filtered through 0.2 μm millipore filters and dialysed against TE (10 mM Tris-HCl, 1 mM EDTA, pH 8.0). To inhibit protease activity EDTA and PMSF were added to the dialysis bag to final concentrations of 1 mM and 0.1 mM respectively. Proteins were precipitated for SDS PAGE by the addition of trichloroacetic acid to a final concentration of 10% at 0° C. After centrifugation the protein pellet was suspended in 1 M Tris base and then mixed with an equal volume of 2×SDS sample buffer for polyacrylamide gel electrophoresis.

6. Fractionation of Lactococcus.

Lactococci were recovered from medium by centrifugation following the addition of NaCl to a final concentration of 1 M. The cells were washed twice in Wash Buffer (WB: 100 mM Tris-HCl pH 7.5, 5 mM $MgCl_2$, 2 mM EDTA, 1 mM PMSF) and each gram of cells (wet weight) resuspended in about 3–4 ml of ice cold WB containing protease inhibitors. The cells were homogenised with 40–50 g of glass beads (0.10–0.11 mm diameter) in a Braun cell homogeniser (model MSK) for 2×30 sec with the $CO_2$ cooling system in operation. The glass beads were removed by filtration through a coarse sintered-glass filter and the homogenate centrifuged at 10,000 g for 15 min to pellet the cell walls. The membranes were removed from the soluble protein fraction by centrifugation at 144,000 g for 75 min at 4° C. Protein concentration was estimated by the bicinchoninic acid assay (Pierce Europe Inc) using BSA as the standard.

7. Immunoblotting and ELISA

Proteins from total cell extracts and culture supernatants were separated by SDS PAGE and electroblotted onto nitrocellulose.[28] The transfer of protein was checked by reversibly staining the filter with Ponceau S, after which the TTFC was detected by the use of a rabbit anti-TTFC antiserum and alkaline phosphatase-conjugated goat anti-rabbit immunoglobulins (Nordic Immunological Labs U.K). For the TTFC ELISA the microtitre plates were coated with standard amounts of purified TTFC as well as soluble protein extracts and supernatants from the control and expressing strains (in 100 μl) by incubating for 3 h at 37° C. and then overnight at 4° C. The plates were then blocked by adding 150 μl of blocking buffer (PBS containing 0.05% Tween 20 and 0.5% BSA), washed once with PBS/0.05% Tween and then incubated with rabbit anti-fragment C antiserum (diluted in blocking buffer) for 2 h at 37° C. The plates were washed 4 times in PBS/Tween and then incubated with the alkaline phosphatase-conjugated goat anti-rabbit immunoglobulins (Nordic) for 1–2 h at 37° C. The plates were then washed 4 times in PBS/Tween and finally in PBS before developing with OPD.

8. Construction of T7 expression shuttle vectors for use in *Lactococcus lactis*.

The EcoRV/BglII fragment from pET-3a containing the bacteriophage T7 promoter of gene 10, its translation initiation region and transcription termination signal[8] was purified and ligated into p18N (see Table 1) cut with BamHI and HincII (see p18NT7 FIG. 1). Competent *E. coli* 'SURE' cells were transformed with the ligated DNA and individual clones picked and tested for the recombinant plasmid as described in Materials and Methods.

Plasmid p18NT7 was modified for expression and secretion in *Lactococcus lactis* by replacing the T7 bacteriophage gene 10 translation initiation region with the ribosome binding site and signal leader sequence of the serine proteinase of *Lactococcus lactis*. The relevant proteinase (prt gene DNA fragment was obtained by PCR amplification using primers with 5' extensions containing restriction endonuclease sites for either HindIII or BamHI. A SalI restriction site was also included in the 5' overhang of the anti-sense primer to allow gene fusions to be made to the prt leader. A SalI restriction endonuclease site can also be cleaved by AccI or HincII thereby allowing gene fusions to be made in any of the three reading frames. (Sequences of the primers are given above.) The PCR amplified DNA was cut with HindIII, then blunted with T4 DNA polymerase and cut with BamHl. The digested fragment was gel purified and ligated to p18NT7 cut with XbaI and blunted and then cut with BamHl to generate p18NT7LVF. Competent *E. coli* "SURE' cells were transformed with the ligated DNA and individual clones picked and tested for the presence of the correct insert by restriction enzyme digestion and agarose gel electrophoresis. A plasmid map of clone p18NT7L1VF (L1VF= signal leader 1; variable frame) and details of the sequence constructions can be found in FIG. 1 and FIG. 2 respectively.

Figure 2:
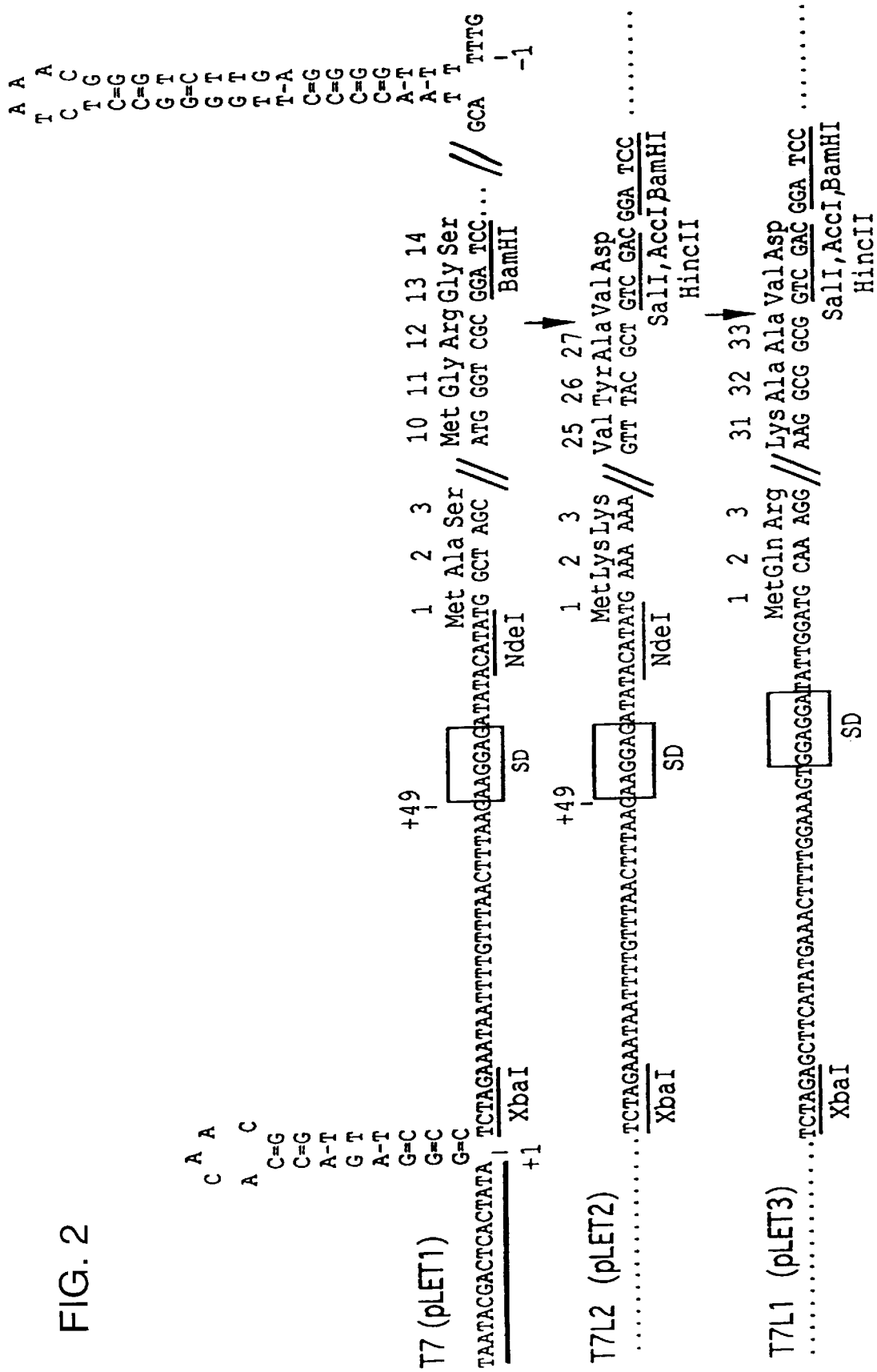

A second lactococcal signal leader of the 45 kD unknown secreted protein (usp45) of *Lactococcus lactis*[29] was synthesised using long overlapping oligonucleotides which were annealed and extended using T7 DNA polymerase. The double stranded product was cut with NdeI and BamHl, gel purified and ligated to NdeI and BamHl cut p18NT7 to generate p18NT7L2VF (see FIG. 1; L2VF=signal leader 2; variable frame). This signal leader replaced the T7 bacteriophage gene 10 coding sequence in p18NT7 without altering the nucleotide spacing between the ATG start codon and the Shine Dalgarno sequence as shown in FIG. 2. As for leader 1 the last amino acid of the signal peptide proceeds a SalI restriction site to allow gene fusions to be made in any of the three reading frames.

Figure 3A:
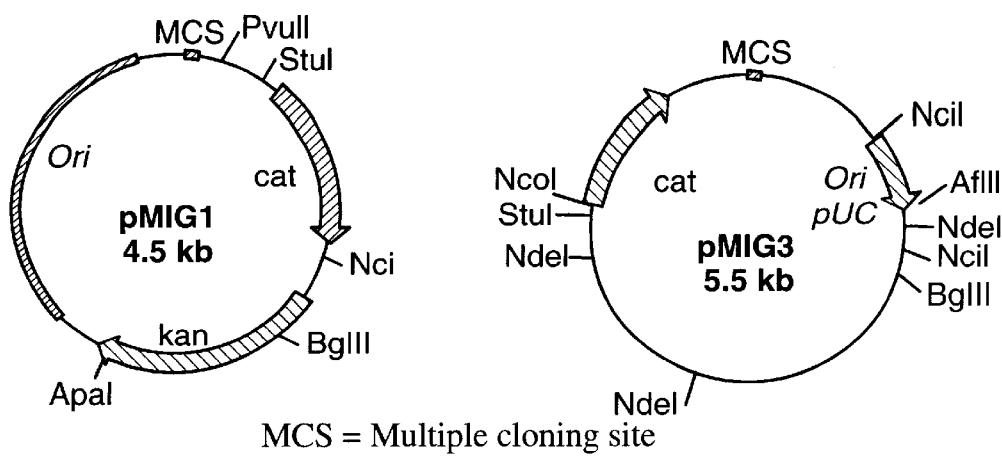
Figure 3B:
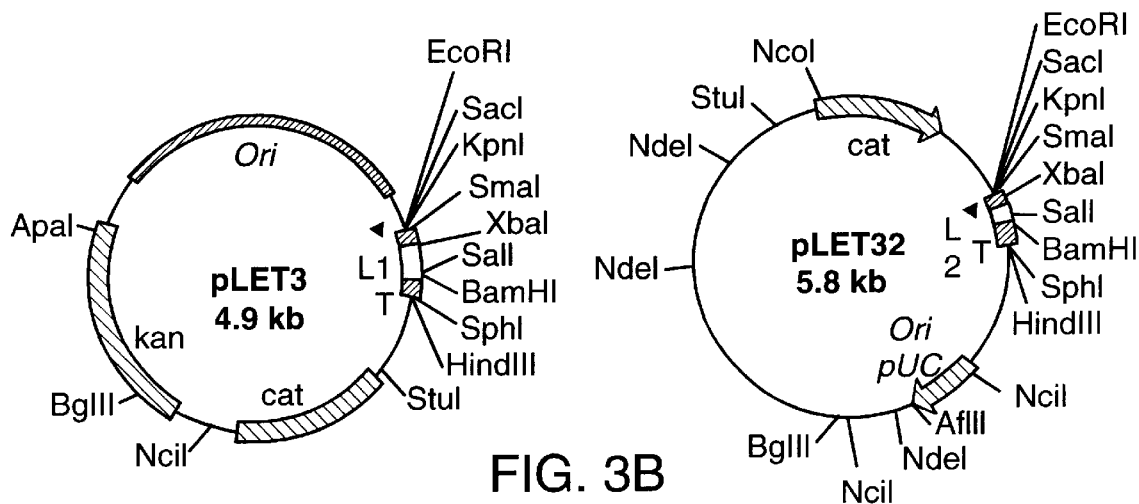

In order to express foreign genes in *L. lactis* using the modified sequences for expression with T7 RNA polymerase described above it was necessary to transfer the EcoRl and HindIII fragment of p18NT7LVF and p18NT7L2VF to shuttle vectors which will replicate in *L. lactis*. Two shuttle vectors for cloning in *E. coli* and *L. lactis* pMIG1 and pMIG3 were recently constructed which have different copy numbers in *L. lactis* (FIG. 3). pMIG1 contains the pSH71 replicon of *L. lactis*[30], replicates at high copy number in *L. lactis* strain MG1363 (about 100 copies per bacterium in a stationary culture) and is capable of replication in Rec A+ *E. coli* and *B.subtilis*. Plasmid pMIG3 is a low copy number vector in *L. lactis* (several copies per bacterium in stationary culture) but replicates at high copy number in all the commonly used laboratory strains of *E. coli*. The plasmids pMIG1 and pMIG3 were cut with EcoRl and HindIII and ligated to the EcoRl-HindIII cut fragments of p18NT7L1VF and p18NT7L2VF. The resulting plasmids for cloning and expressing target DNAs under control of a T7 promoter in Lactococcus are designated pLET vectors plasmid for Lactococcal expression by T7 RNA polymerase). Plasmids pLET3 and pLET2 are pMIG1 vectors containing the T7 expression cassettes from p18NT7L1VF and pl8NT7L2VF respectively; pLET33 and pLET32 are pMIG3 vectors containing the T7 expression cassettes from p18NT7L1VF and p18NT7L2VF respectively (see FIG. 3 for examples).

The T7 expression cassette in p18NT7 was also removed from the plasmid p18N as an EcoRl-HindIII fragment and ligated to the EcoRl and HindIII cut shuttle vector pMIG1 to generate the vector pLET1 which lacks a signal secretion sequence The sequence of this expression cassette (SEQ ID NOS: 1–4) is also shown in FIG. 2.

9. Construction of a Lactococcal vector for Inducible Expression of T7 RNA Polymerase.

In order to over-express foreign genes in bacteria it is necessary to have an inducible system, otherwise the products may be sufficiently toxic to prevent isolation of the recombinant strains. Furthermore, a regulated expression system allows the expression strains to be grown and maintained under conditions which are minimally selective for organisms which might otherwise escape expression by spontaneous mutation or by loss of the recombinant plasmids. To allow for these possibilities the T7 RNA polymerase gene was placed under the control of the recently reported *Lactococcus lactis* lactose inducible promoter which regulates expression of the lactose operon genes.[31,32]

Figure 4:
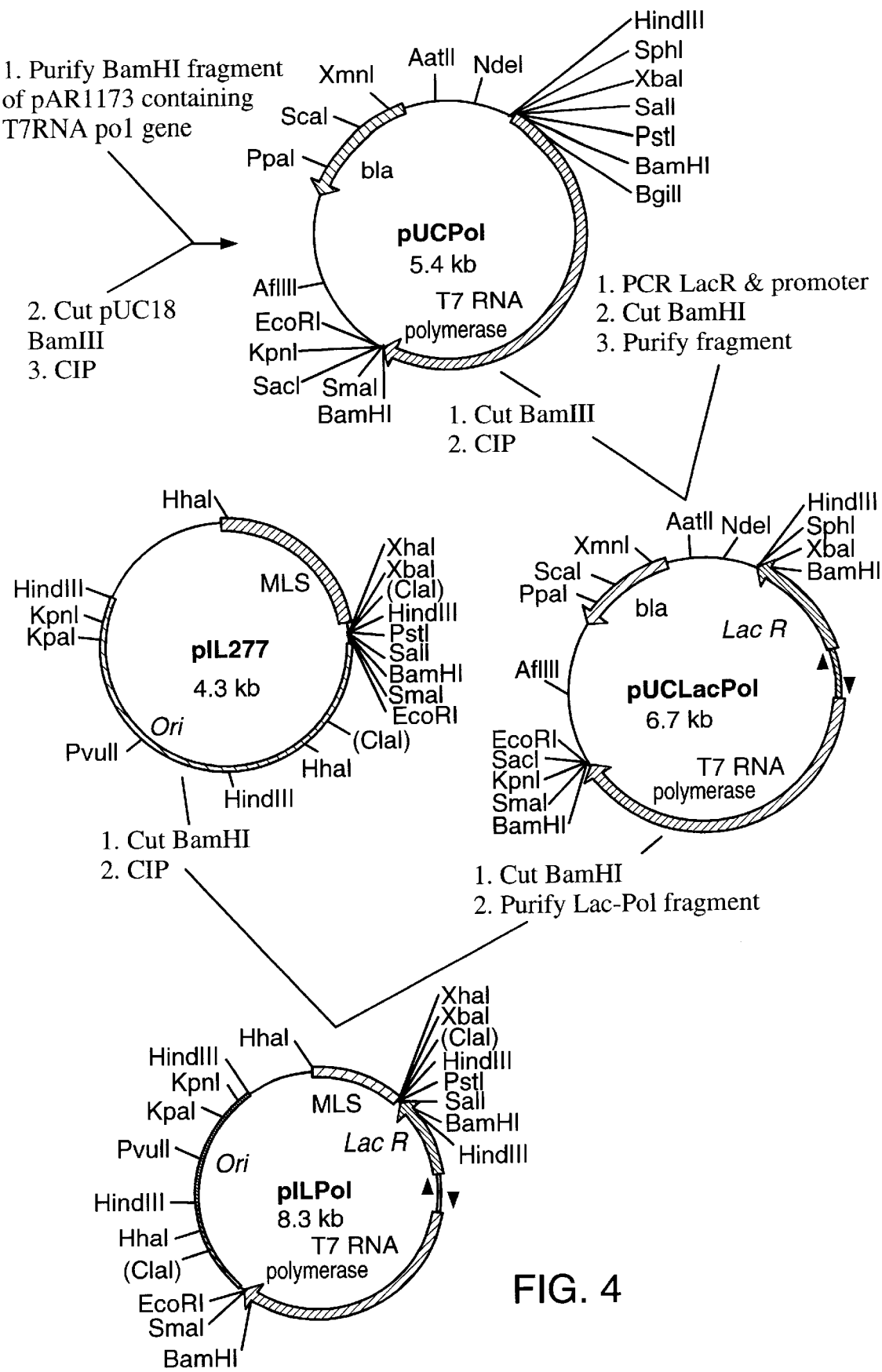

The T7 RNA polymerase gene in plasmid pAR1173 (Table 1) is located on a 2.7 kb BamHl fragment comprising the entire gene and 24 nucleotides upstream of the translation start codon containing the Shine Daigarno (SD) motif required for translation initiation. To facilitate further cloning procedures the BamHl fragment from pAR 1173 was cloned into the BamHl site of pUC18 to generate pUCPol (FIG. 4). The BamHl site at the 5' end of the gene precedes at BglII site at which the the lac promoter and repressor gene were inserted. The lac promoter and its repressor were isolated by PCR amplification using primers with a BamHl site at the 5' end so that after ligation to BglII cut pUCPol the SD of the T7 RNA polymerase replaced the SD of the lac operon promoter sequence (see pUCLacPol FIG. 4).

The Lac repressor (LacR), and T7 RNA polymerase gene under control of the regulated *L. lactis* lac promoter was isolated and purified from BamHl cut pUCLacPol and ligated to BamHl cut pIL277 (FIG. 4). The resulting plasmid (pILPol) is low copy (several copies/cell) in *L. lactis* and confers resistance to erythromycin. Finally, a host strain for expression by T7 RNA polymerase was established by transforming strain MG1820 with pILPol. Strain MG1820 carries a large 23.7 kb plasmid containing the genes required for growth on lactose (Table 1).

10. Cloning of Tetanus Toxin C Fragment in *L. lactis* Expression Vectors.

The tetanus toxin gene fragment C (TTFC) which is non-toxic and involved in ganglioside binding of the holotoxin to animal neuronal cells has been cloned and produced in *E. coli*. We have used this gene fragment as a test protein for expression in *L. lactis* because it is derived from a Gram-positive bacterium and can be easily detected by Western blotting and ELISA.

Figure 3C:
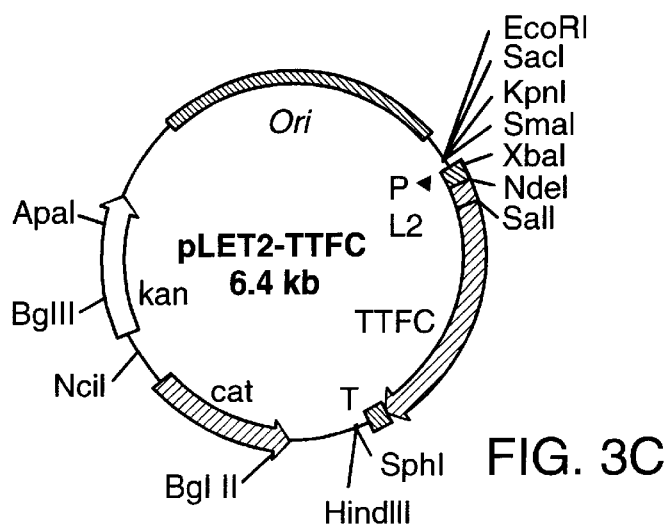

The gene for TTFC can be removed from the *E. coli* TTFC expression vector pSS1261 (Table 1) by digestion with SalI and PstI. This plasmid was therefore cut with PstI, the DNA blunt-ended with T4 DNA polymerase and then cut with SalI. This gene fragment was purified from an agarose gel and ligated to BamHl cut, blunted and SalI cut pLET3, pLET2, pLET33 and pLET32 (an example of which is shown in FIG. 3C).

The DNA fragment encoding TTFC was also cloned into the BamHl site of pLET1 to generate an expression plasmid pLET1-TTFC; the reading frame was preserved with respect to the first 33 nucleotides of the T7 gene 10 so that it was in frame with the first 11 amino acids of the T7 bacteriophage gene 10 protein. In order to achieve this a DNA fragment encoding TTFC was amplified by PCR using a sense primer with a restriction site for BglII at its 5' end, and an antisense primer with a BamHl site at its 5' end. The cohesive ends generated by cutting the PCR fragment encoding TTFC with BglII and BamHl are said to be compatible and can both be ligated into the BamHl site in pLET1. However, the BglII-BamHl ligated ends can not be re-cut with either enzyme. This cloning strategy permits the pLET1-TTFC construct to be re-cut with BamHl only at the 3' end of the TTFC gene thereby providing a unique cloning site which can be used to make gene fusions to TTFC.

The T7 expression vectors containing TTFC in frame with the first 11 amino acids of the T7 bacteriophage gene 10 protein (pLET1-TTFC) or with either signal leader 1 or signal leader 2 were transferred to the *L. lactis* host strain for T7 expression (MG1820, pILPol: Table 1) by electroporation. The host strain was also transformed with the vectors pMIG1 and pMIG3 to provide controls for the ensuing experiments.

11. Expression of Tetanus toxin Fragment C in *L. lactis*.

The recombinant clones for expression of tetanus toxin fragment C, and the control strains were grown to an optical density at 600 nm ($OD_{600\ nm}$) of about 0.5 in glucose medium (GM17). Expression of the TTFC gene was then induced by pelleting the cells and resuspending them in lactose medium (LM17) to an $OD_{600nm}$ of about 0.3. Total cell protein extracts and TCA precipitated protein samples from the culture supernatants were prepared at different times after induction.

Figures 5A, 5B:
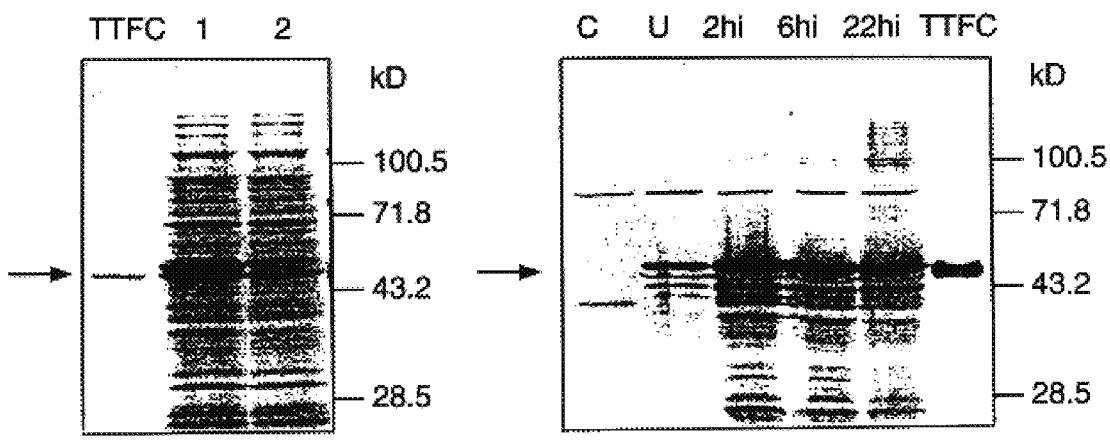

In a Coomassie stained gel of total protein extracts from pLET1-TTFC prepared two hours after induction TTFC was the most abundant protein detected (FIG. 5*a*). This protein was not detected in extracts prepared from the control strain two hours after induction. The results of Western blotting with total cell protein extracts prepared from the pLET1-TTFC strain confirmed that TTFC was expressed in induced cells. It was also expressed at low levels in uninduced cells (FIG. 5*b*).

Figure 5C:
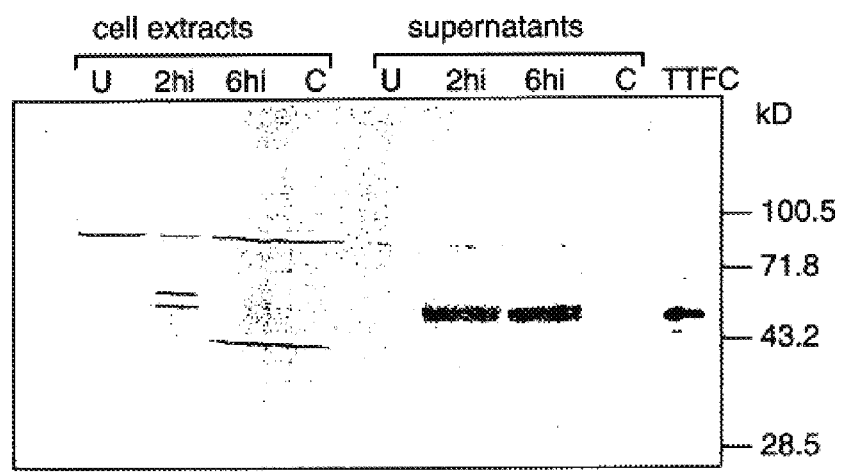
Figure 5D:
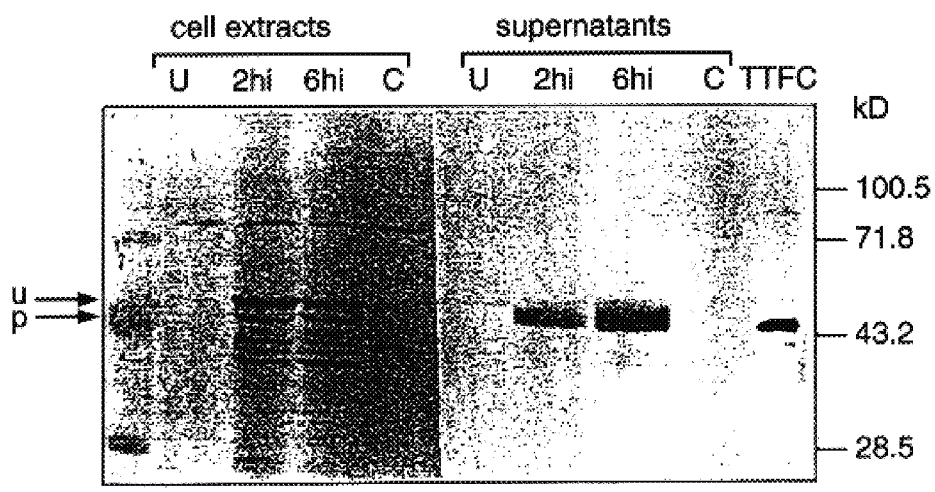

The results of immunoblotting total cell extracts and proteins precipitated from the culture supernatants of the expression-secretion strains (pLET3-TTFC and pLET2-TTFC) with TTFC antiserum also indicated that induction of TTFC gene expression by lactose led to the formation of TTFC (FIG. 5*c* & *d*). Furthermore, both signal leaders were able to mediate secretion of TTFC into the culture medium. However, the two strains differed with respect to the amounts of TTFC detected in the total cell extracts; TTFC was only detected in low amounts in pLET3-TTFC and only at 2 h after induction whereas substantially more TTFC was detected in the cell extracts of the pLET2-TTFC strain. A marked feature of all the immunoblots was the detection of a high molecular weight species of TTFC in the total cell extracts of these cells. This product is most likely to be the unprocessed (signal sequence+TTFC) form of the protein (arrowed in FIG. 5*d*) In contrast the results obtained with the signal leader 1 fusion construct (pLET3-TTFC) showed that TTFC did not accumulate in the cytoplasm of these cells, but was co-translationally secreted into the growth medium (FIG. 5*c*). No TTFC was detected in the total cell extracts or culture supernatants of the pMIG1 control strains.

Figure 6A:
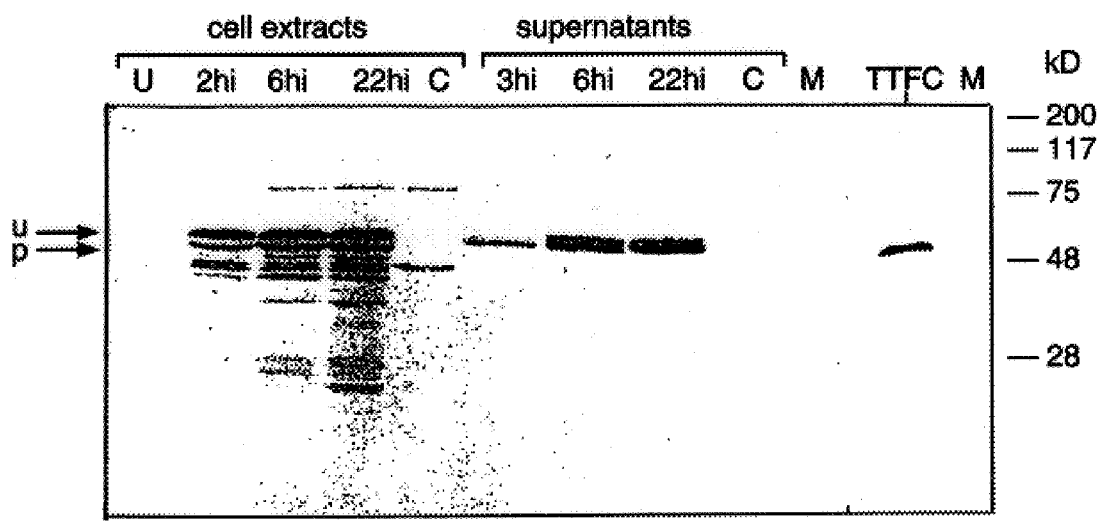
Figure 6B:
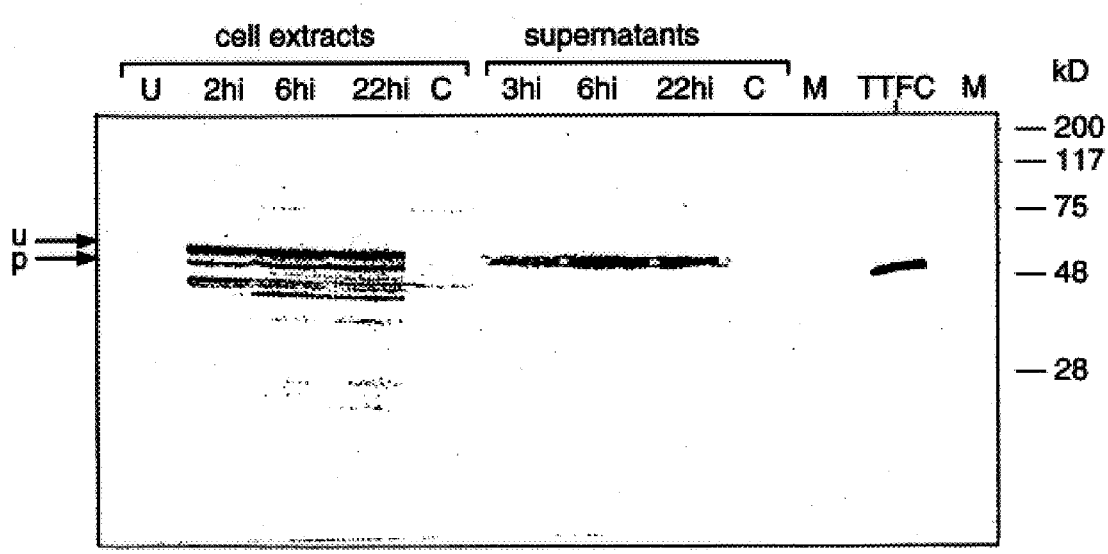

The levels of TTFC produced by the low and high copy expression secretion vectors carrying the T7L2 expression cassette (pLET2-TTFC and pLET32-TTFC) were compared by immunoblotting. The results of Western blots with anti-fragment C serum to total cell protein extracts and proteins precipitated from the culture supernatants of these strains is shown in FIG. 6*a* and 6*b* respectively. As above the results show that TTFC was detected in the cell extracts and culture supernatants of this strain following induction by lactose. No TTFC was detected in extracts of these cells grown in glucose or in the control strains. Strikingly there was little difference in the apparent levels of expression between the low copy and high copy number vectors carrying the target gene.

12. Assay of TTFC in Culture Supernatants and Soluble Protein Extracts of *Lactococcus lactis.*

Cells from the expression strain pLET1-TTFC (which lacked any secretion signal leader) and from pLET2-TTFC (secretion leader 2) were disrupted 1.5 to 2 hours after induction by mechanical homogenisation. Several dilutions of the protein extracts (in duplicate) and of purified rTTFC from *E. coli* (in duplicate) were used to coat a microtitre plate for an ELISA. The amounts of TTFC in the soluble extracts of these strains were determined from the standard curve, and the percentage of TTFC as soluble protein in the extracts of pLET1-TTFC and pLET2-TTFC was calculated to be 22% and 3.4% respectively. No TTFC was detected in the soluble extracts from the control strain (which harboured the pMIG1 vector lacking the T7 expression sequences and TTFC gene).

Five micrograms of soluble protein and a proportional amount of the washed insoluble fraction from each strain was analysed by SDS PAGE and Western blotting with anti-TTFC. The results (FIG. 7) show that TTFC is detected only in pLET2-TTFC and not in the control strain. Interestingly, TTFC is also evident in the insoluble fraction from the expressing strain suggesting that the protein might have aggregated in the cell to form insoluble inclusion-like bodies.

In order to determine the amounts of TTFC secreted by the *L. lactis* strains pLET3-TTFC and pLET2-TTFC the cultures were induced and the culture supernatants (taken at different times after induction) assayed for TTFC by an ELISA. FIG. 8*a* shows that these strains reached stationary phase of growth approximately 4 hours after induction and that the pLET2-TTFC strain grew more slowly than did cells which carried pLET3-TTFC or the pMIG1 control and did not reach the same final cell density. When TTFC secretion was assayed over a 6 h time course following induction (FIG. 8*b*) the amounts of TTFC secreted into the growth medium by the strain which carried pLET3-TTFC reached a plateau (approximately 1 $\mu$g/ml) when the cells entered stationary phase. The quantities of TTFC secreted into the growth medium by pLET2-TTFC were higher (approximately 2 $\mu$g/ml after 6 h). TTFC was not detected in the supernatants of the pMIG1 control strain.

In view of the slower growth rate of pLET2-TTFC strain compared to the pLET3-TTFC and the pMIG1 control strain the numbers of dead cells present at different times after induction were determined by adding propidium iodide (PI; 10 mg/ml) to dilutions of the cultures in PBS, and the cells examined by phase contrast and fluorescence microscopy. The results indicated that less than 0.5% of the bacteria in the pLET3-TTFC and control strain were permeable to PI 6 h after induction. Approximately 5% of the bacteria in the pLET2-TTFC culture became permeable to PI after 2 h and this proportion increased to approximately 10% at 6 h. This suggests the possibility that some of the TTFC detected in the growth medium of this strain could have leaked out from dead cells.

Since the growth and viability of the pLET3-TTFC strain was unaffected following the induction of TTFC production this strain was induced at low cell density and its rate of growth and TTFC secretion monitored over 6 hours. These results showed that the amount of TTFC secreted into the growth medium was proportional to the cell density (FIG. 8*c*). During the exponential phase of growth the amounts of TTFC secreted into the growth medium was calculated to be approximately 2 $\mu$g/ml/hour.

13. Discussion of expression results

These results demonstrate for the first time that it is possible to construct a system for the regulated expression, and optionally secretion, of substantial quantities of a heterologous gene product in *Lactococcus lactis.*

In our system gene expression can be induced by the addition of lactose to the growth medium, although the mechanism by which the inducer is formed differs from that found in the well-known lac operon of *E. coli*, since the pathways for the catabolism of lactose are known to be very different in the two organisms. In order that the inducer metabolite of lactose would be formed we used a strain of *L. lactis* (MG1820) which carries a 23.7 kb low copy number plasmid encoding the lactococcal lac operon. The expression strain of *L. lactis* was also transformed with a recombinant low copy number plasmid (plLpol) which carried the T7 RNA polymerase gene under the control of the lactococcal lac promoter. The inducer prevents a repressor molecule blocking transcription at this promoter, and the consequence is that T7 RNA polymerase is made in the cell. The T7 RNA polymerase has such a tight specificity for its cognate promoter sequence (present in this case on the DNA of the target gene plasmid: pLET vector family; see FIG. 2 & 3c) that it initiates transcription, and transcribes the target gene RNA The host cell protein translation and secretion machinery then produces the heterologous protein, and secretes it if the protein has a secretion signal sequence. Our target gene vectors incorporate a replicon which will replicate in a large number of Gram-positive bacteria, including all species of lactic acid bacteria, a number of bacilli, several streptococcal species, Clostridia, Listeria, and *E. coli*. Hence, the vectors described here may be useful for the development of T7 based expression systems in these other organisms.

The gene for TTFC was cloned into the expression vector pLET1 and high and low copy number pLET vectors into which one of two different secretion leader sequences had previously been cloned (L1 & L2). Subsequently the *L. lactis* expression host (by then carrying the lactose operon plasmid 1820 & plLpol) was further transformed with the target gene plasmids. When these cells were induced gene expression mediated by the regulated production of T7 RNA polymerase was observed. No TTFC protein was detected in the supernatants or cytoplasmic fractions of a pMIG1 control strain. The pLET1-TTFC strain produced approximately 22% of soluble protein as TTFC after just two hours induction. Both the secretion signal sequences used directed the secretion of TTFC into the growth medium, but TTFC was only found in substantial amounts (3.4% of soluble protein) in extracts from the pLET2-TTFC strain, in which the lactococcal usp45 signal leader (L2) was used to direct secretion. Since similar amounts of TTFC were secreted by cells which carried either of the two signal leaders the intracellular accumulation of TTFC in the pLET2-TTFC strain was probably a consequence of higher levels of expression. This result was surprising. It had been expected that the pLET3-TTFC strain might produce more protein than the pLET2-TTFC strain, since in the T7L1 expression cassette all the sequences downstream of the T7 promoter and RNA stabilizing sequence including the ribosome binding site are of lactococcal origin. The reasons for the lower levels of gene expression seen with the pLET3-TTFC construct are unknown. One possibility is that the 5' secondary structure sequence and the Shine-Dalgarno sequence of the two mRNA's promote protein translation initiation at different rates. These factors might also account for the higher levels of TTFC expression obtained with the pLET1 vector compared to the expression-secretion vectors pLET3-TTFC and pLET2-TTFC.

Immunoblotting of extracts of the soluble and insoluble proteins of the expression strain harbouring pLET2-TTFC; prepared two hours after induction showed that most of the TTFC recovered in the soluble protein fraction was of a lower molecular weight than the TTFC associated with the insoluble fraction. This difference in molecular weight implied that intracellular soluble protein had been processed to its secreted form, whilst intracellular insoluble protein remained unprocessed. This suggests that nearly all of the TTFC recovered as soluble protein from in the cell has been membrane translocated and probably lies between the cytoplasmic membrane and the cell wall. If this is in fact the case the rate of diffusion of TTFC through the cell wall must be the rate limiting step in protein secretion, at least under the growth conditions used here by us. The TTFC detected in the insoluble fraction by SDS PAGE and immunoblotting might arise from the aggregation and precipitation of protein in the cell as commonly observed for other recombinant proteins which have been over-expressed in *E. coli*. Alternatively, this unprocessed form of TTFC might arise from cell membrane which has remained associated with the cell wall during fractionation.

The TTFC detected in the soluble and insoluble fractions of mechanically homogenized cells was apparently undegraded while some degradation was evident in total cell extracts prepared by a slow extraction procedure involving the incubation of cells with lysozyme and mutanolysin at 370° C. It is likely that the enzyme digestion of the wall and the subsequent washing steps in the absence of any protease inhibitors activated degradative processes in dying cells. The TTFC secreted into the growth medium of cultured cells by our expression-secretion strains remained undegraded even after incubation for 22 hours. These results encourage the belief that protease degradation will not impede the use of *L. lactis* for heterologous protein production.

In our experiments the cells were induced during the mid-exponential phase of growth and reached stationary phase about 3–4 hours after induction. An accumulation of intracellular protein was not detected in total cell extracts at 6 or 22 hours after induction, although the amounts of TTFC secreted into the growth medium increase about 10–20 fold during this time. In light of the above results it seems most likely that expression by T7 polymerase is limited or inhibited when cells enter the stationary phase of growth and that the amounts of TTFC secreted into the growth medium increase with time as the protein diffuses through the cell wall.

The growth and viability of one of our expression—secretion strains (pLET3-TTFC) was identical to that of the pMIG1 control stain even when grown from low cell density in the presence of the inducer. In the exponential phase of growth this strain secreted approximately 2 $\mu$g of 7TTFC per hour into the growth medium.

A further improvement to our expression system would come from eliminating the need for antibiotic-mediated selection for the plasmid-borne lac promoter & T7 RNA polymerase sequences by integrating these into the chromosome of an *L. lactis* host strain. Expression cassettes incorporating the target gene could also be integrated into the host genome for similar reasons. Our recent results imply that such integration would be unlikely to diminish product yield. We have found that similar amounts of TTFC were produced by both low and high copy number TTFC expression vectors which implies that maintenance of a high copy number of the target gene is not required for the system to yield substantial quantities of target gene product. These results also give reason to believe that in addition to its potential use for vaccine antigen delivery *L. lactis* could be further developed as a safe and useful addition to the group of microorganisms which can be used for the production and secretion of recombinant proteins in soluble form.

14. In vivo data—Immune responses

General

Mice were immunised by subcutaneous or oral administration of recombinant *L. lactis* cells expressing TTFC. The cells were induced with lactose for 2 hours, then washed and resuspended in 100 $\mu$l PBS for subcutaneous administration of 0.2 M sodium bicarbonate for oral administration.

Experiment 1: subcutaneous administration (pLET2-TTFC)

Balb/c male mice, 5–6 weeks old at the start of the experiment, were divided into four groups, each of six animals.

Group 1: received on each of days 0 and 1 subcutaneous inoculation of >1×10$^9$ recombinant *L. lactis* cells expressing 7TTFC from the pLET2-TTFC vector.

Group 2: received on each of days 0 and 1 subcutaneous inoculation of >1×10$^9$ *L. lactis* which did not express TTFC (i.e. negative control to distinguish over any effect due to the administration of *L. lactis* per se).

Group 3: received on each of days 0, 15 and 58 subcutaneous inoculation of 10 μg of commercially available TTFC fragment C in PBS (i.e. positive control comparison of TTFC in available purified TTFC conventionally used for immunisation).

Group 4: received no inoculation (i.e. straight negative control).

All four groups were challenged on day 65 with a single subcutaneous dose of tetanus toxin of approx 2–4 LD$_{50}$, and were examined 24 hours post-challenge.

In the two negative control groups (2 and 4), all six animals showed obvious symptoms of paralysis (and were humanely dispatched as required by law). In both the positive control group (3) and the *L. lactis* TTFC group (1), all animals were free of symptoms at 24 hours p.c., although one animal in group 1 showed mild paralytic symptoms after 72 hours.

These results show that TTFC expressed and contained intracellularly in *L. lactis* is in a biologically active conformation capable of giving a protective effect against the pathogen similar in kind to that obtained by conventionally used purified TTFC when administered subcutaneously. Also, it shows that the immunogenicity of antigens expressed in *L. lactis* is not limited only to antigens originating from closely related bacterial species such as Streptococci (iwaki et al.).

Experiment 2: subcutaneous administration (pLET1-TTFC vs pLET2-TTFC)

This experiment compares the protective effect of the pLET2-TTFC expression product (see Experiment 1) with the pLET1-TTFC expression product. As shown above; whereas pLET2 is a secretory construct which nevertheless retains TTFC intracellularly at about 3.4% of soluble protein, pLET1 is not a secretory construct and TTFC accumulates intracellularly to about 22% of soluble proteins.

CBA mice were inoculated subcutaneously three times at two-weekly intervals. Those mice showing significant increases in serum antibody were challenged with purified tetanus toxin subcutaneously 14–20 days after the last inoculation.

For each TTFC construct, the mice were divided into three groups, receiving respectively $5\times10^6$, $5\times10^7$ and $5\times10^8$ recombinant *L. lactis* cells. For challenge, each of these groups was divided into two sub-groups, receiving respectively $20\times LD_{50}$ and $5\times LD_{50}$ tetanus toxin. The results are shown below.

| | | | |
|---|---|---|---|
| pLET2-TTFC | $5\times10^6$ | 0/4 | 0/3 |
| | $5\times10^7$ | 0/4 | 0/3 |
| | $5\times10^8$ | 4/4 | 3/3 |
| pLET1-TTFC | $5\times10^6$ | n/d | n/d |
| | $5\times10^7$ | 4/4 | 3/3 |
| | $5\times10^8$ | 4/4 | 3/3 |

These results show that the high-level intracellular expresser pLET1-TTFC *L. lactis* strain is approximately 10-fold more effective at providing protection than the lower-level intracellular expressor pLET2-TTFC. In other words, despite being expressed intracellularly at a very high level in the *L. lactis* cells, the TTFC protein nevertheless appears to assume more or less fully its conformationally active state (since B-cells respond to conformational epitopes) for providing a protective effect; a result strikingly different from that commonly found when heterologous polypeptides are expressed at high levels in *E. coli*, for example.

In other experiments (data not shown) by comparing the TTFC *L. lactis* inoculation dosage level required to achieve a fully protective level of antibody in different strains of (Balb/c and C57BL/6), it was found that the pLET1-TTFC *L. lactis* strain was more effective than the pLET2-TTFC strain, to the extent that, for a given dosage level (no. of cells) it required one less dose to reach that protective antibody level, or for a given number of doses the protective antibody level was achieved with a 10-fold lesser dosage level (no. of cells). In short, these data tend to confirm the inferences drawn above from the CBA data.

Experiment 3: oral administration

C57BL/6 mice were orally inoculated with *L. lactis* strains pLET2-TTFC and pLET1-TTFC. Three mice per group were used. Groups of mice were orally inoculated (under ether anaesthetic) with the following doses of *L. lactis* strains resuspended in 0.2M sodium bicarbonate buffer:

Group 1: $5\times10^8$ pLET2-TTFC
Group 2: $5\times10^9$ pLET2-TTFC
Group 3: $5\times10^8$ pLET1-TTFC
Group 4: $5\times10^9$ pLET1-TTFC
Group 5: 100 ml sodium bicarbonate alone.
Group 6: $5\times10^9$ pMIG1 (non-TTFC expressor strain)

The immunisation regime was as follows:

Day 1: Blood sample obtained from tail vein
Day 3: Oral inoculation of mice
Day 11: Blood sample obtained from tail vein
Day 25: Blood sample obtained from tail vein
Day 32: Oral inoculation
Day 39: Blood sample obtained from tail vein
Day 83: Blood sample obtained from tail vein
Day 90: Blood sample obtained from tail vein
Day 97: Blood sample obtained from tail vein Blood was stored overnight at 40° C., centrifuged at room temperature for 5 minutes and serum transferred to a sterile tube. Sodium azide was added to a concentration of 0.02M and the samples stored at −20° C. until required. No additional adjuvant was used for inoculation.

Systemic (serum) antibody (IgM and IgG) to tetanus toxin was detected from the blood samples in an ELISA assay using tetanus toxoid as the antigen.

For mucosal antibody (IgA), the samples were equalised to 1 mg/ml of total IgA prior to determination of the anti-TTFC antibody titre.

The results showed that the mice in group 4, which had received $5\times10^9$ pLET1-TTFC *L. lactis* cells (the high-level non-secreting strain), gave significantly raised levels of anti-TTFC soluble IgA after the third inoculation. No significantly raised levels of IgA were detected in any of the other groups.

As regards IgG and IgM, preliminary results suggest a significantly raised anti-TTFC IgM level from group 2, with a lesser response from group 4; while the observed IgG levels remained low, but with a possibly significant increase in group 2 again.

These results clearly indicate a positive mucosal response from the oral administration of 7TTFC contained intracellularly within the *L. lactis* cells. This compares with the straight oral administration of 7TTFC (with or without adjuvant) which is not known to produce any significant immune response, and indicates an important effect from the cellular encapsulation in getting the TTFC expression product to the appropriate location for inducing a mucosal immune response, and of course still in an immunologically active configuration.

So far as the systemic immune response is concerned, if the preliminary data so far are confirmed and optimised, it may indicate that the effect is associated with lower levels of immunogen (eg the low-expressor pLET2 strain rather than the higher expressing pLET1 strain), or with in vivo secretion of TTFC from the cells (again, secretory pLET2 vs non-secretory pLET1).

General remarks on the in vivo data

These results show for the first time the expression in Lactococcus of a non-streptococcal (non-lactococcal) antigen which, when administered orally, produces an immune response.

They also show that a heterologous protein can be expressed in Lactococcus and accumulated intracellularly at high levels as soluble protein in a biologically active conformation. In particular, this enables immunogenic proteins to be delivered in the protective environment of the expressing cell to a subject to be immunised, thereby opening up new possibilities for vaccine production and delivery systems.

Example 2

3. Expression of membrane anchored proteins in *L. lactis*

Construction of an expression vector for the membrane anchoring of antigens and other proteins in *L. lactis* Since it is known that some antigens are most potent if their epitopes are exposed at the surface of readily phagocytosed particles such as bacteria we have developed a procedure which permits an antigen such as TTFC to be anchored in the plasma membrane of *L lactis*.

This was done by creating a fusion protein incorporating the membrane anchoring domain of the lactococcal cell-wall associated proteinase gene from *L. Lactis* as a C-terminal fusion to TTFC. The expression vector was constructed in the following way 1. A DNA fragment encoding the cell-wall and membrane anchoring domain of the proteinase (Prt) gene of *L. lactis* strain NCDO763 (nt 6518 to 6913) was obtained by PCR amplification using appropriate primers based on the published sequence.[34] To facilitate cloning the primers were designed to incorporate BamHl and Bglll restriction sites at the 5' and 3' ends of the gene respectively. 2. The purified PCR fragment so obtained was cloned into the BamHl site of a modified pLET2 vector to generate pLET4. In plasmid pLET4 a unique BamHl restriction endonuclease site lies between the signal leader and the wall-spanning and membrane anchoring domain. It is at this site that target genes can be inserted.

Figures 15A, 15B:
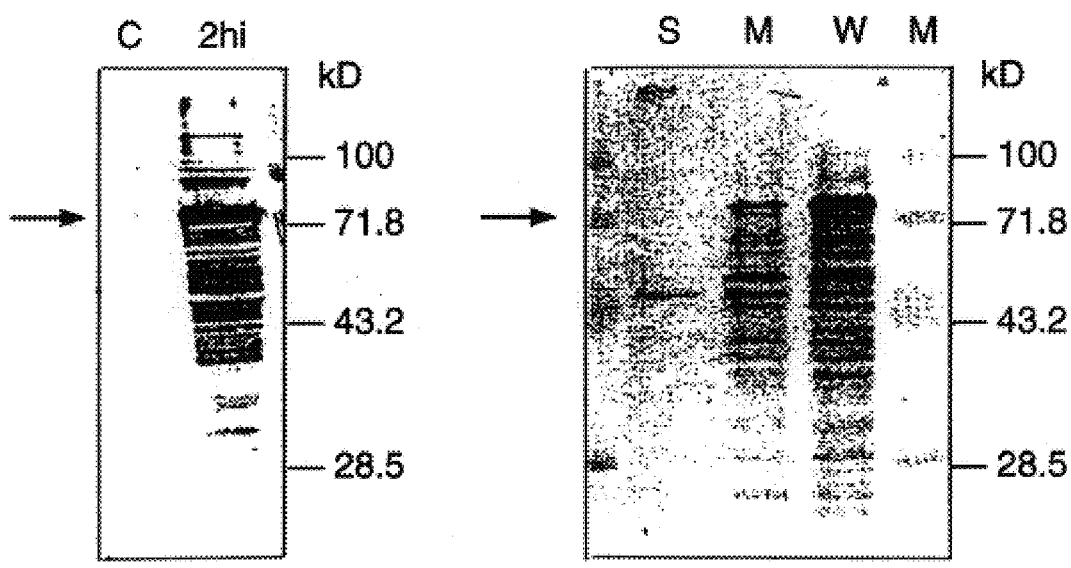

As an example of such a construct we show here that it is possible to derive a cell-membrane anchored version of TTFC. The same PCR derived DNA fragment encoding TTFC that was cloned into pLET1 was also ligated into the BamHl site of plasmid pLET4 to generate pLET4-TTFC. When the expression strains carrying pLET4-TTFC were induced a fusion protein of correct size was seen and could be recognised by anti TTFC antibody (FIG. 15*a*). The results of immunoblotting experiments with sub-cellular fractions of induced cells showed that the fusion protein was not present in in the soluble cytoplasmic fraction and was present in membrane and insoluble fractions (FIG. 15*b*). These results demonstrate that all of the fusion protein produced is intimately associated with the cell membrane.

Example 3

1. Expression of HIV 1 V3 loop, antigen in *Lactococcus lactis*

Introduction

When the human immunodeficiency virus (HIV 1) is transmitted from person to person it commonly infects its host across the mucosal membranes of the male and female genital organs. These mucosal surfaces like others in the body, are bathed by glandular secretions which contain locally produced immunoglobins of the class known as secretory IgA (sIgA). Such immunoglobins are believed to constitute an important first line of defence against infection. It has been observed for a number of diseases that protection against infection is more closely correlated with secretory antibody formation than it is with systemic antibody formation. For this reason methods of stimulating adequately protective and prolonged sIgA responses are of considerable practical importance since they would enable one to develop vaccines which would provide protection against infection rather than protection against disease. Most conventional vaccines available at the present time aim to activate the systemic immune system so that it subsequently limits the multiplication and spread of the infectious agent against which the corresponding vaccine is directed. For most diseases the distinction between protection against infection and protection against disease is not particularly significant. In the case of HIV 1 infection, however, such a distinction is clearly vital since once the virus has inserted its DNA into that of its host cell the infectious process can not be reversed or cured. For any vaccine to provide successful protection against HIV1 it is therefore important that it should elicit a sufficient state of mucosal immunity (and also systemic immunity) for early neutralisation of free virus to occur, thus blocking viral entry into cells. A key feature of any potential HIV vaccine designed to prevent infection is that should be capable of eliciting the formation of adequate quantities of neutralising sIgA.

Studies by other workers have revealed that neutralisation of HIV 1 is a function primarily of antibody mediated reactions directed against the envelope protein of the virus, particularly that protein known as gp120, and within this protein the region known as the V3 loop. This loop has been defined as the principal neutralising determinant. When antibody of adequate affinity binds to the V3 loop the virus is prevented from entering the cell and infecting it. Since neutralisation of the virus can only occur when adequate quantities of sIgA antibody of the correct specificity and affinity are present in mucosal secretions it is necessary to devise methods for stimulating the formation of these antibodies. Although mucosal immunity can be stimulated by ingesting adequate quantities of antigenic protein such a method is normally very inefficient since the majority of any ingested protein is degraded by stomach acid and/or by the proteolytic enzymes present in the gut. The use of the entire gp120 protein for immunization may be undesirable since certain regions of this protein are considered to induce autoantibodies in humans. However, a small protein encoding the isolated V3 loop is unlikely to be of sufficient molecular size to function well as an antigen.

A practical oral vaccine for the stimulation of mucosal immunity to HIV 1 should therefore comprise (a) a means of producing the protective immunogen at reasonable cost, (b)

a means of delivering that immunogen to the mucosal immune system. .We have devised a procedure to express the HIV 1 V3 loop protein in a food grade lactic acid bacterium—*Lactococcus lactis* subspecies lactis. In the present procedure this has been achieved as follows.

Experimental

1. The DNA sequence encoding the V3 loop of the HIV 1 type MN virus was taken as an example and was obtained by designing oligonudeutide primers suitable for use in polymerase chain reactions (PCR) to amplify vira DNA sequences of different lengths each including and encoding the V3 loop sequence. The primers were designed to include a Bglll site and BamHl site at the 5' and 3' ends respectively and incorporated a few nucleic acid substitutions to create codons more consistent with those found in highly expressed lactococcal genes (FIG. 9). PCR amplification of DNA was performed 10 using high fidelity reaction conditions and a thermal cycler (Cambio Ltd, Cambridge, UK). The reaction mixture contained 1×PCR buffer (10 mM Tris-Cl; pH 7.5 @ 70° C., 50 mM KCl), 250 $\mu$M of each deoxynucleoside triphosphate, 0.5 $\mu$M each primer, 1 mM $MgCl_2$, HIV1 type MN infected cell DNA (1 mg at $1\times10^5$ infectious units/ml) and 2.5 units of Taq DNA polymerase (Cetus Amplitaq) in a total volume of 100 $\mu$l . The template DNA was heated for 5 min at 95° C. before the enzyme was added. 30 cycles of PCR amplification were then run under the following conditions: denaturation at 94° C. for 1 min, primer annealing at 50° C. for 1 min, and extension at 72 C. for 1 min, with a final extension at 72° C. for 5 min.

2. The amplified DNA fragments V3a and V3b (see FIG. 9) encoding the type MN V3 loop sequences were cut with Bglll and BamHl, gel purified and ligated into the BamHl site of a vector constructed for the expression and secretion of TTFC in *L. lactis* (pLET2-TTFC-BamHl) so that the V3 loop would be translated as a fusion to 3' end of the TTFC gene. The resulting target gene vector for expression of the TTFC/V3a fusion protein is shown for example in FIG. 10.

3. The plasmids pLET2-TTFC/V3a and pLET2-TTFC/V3b were then introduced into an expression strain of *L. lactis* carrying the other elements of the system for expression of heterologous genes. The essential elements of this system are depicted in FIG. 11.

4. Bacterial cells carrying the target gene expression plasmids and control elements necessary for the expression system to function were induced to produce to the TTFC/V3 fusion proteins by switching from growth on glucose to growth on lactose. Two hours after induction proteins from total cell extracts were separated by SDS PAGE and electroblotted onto nitrocellulose. The transfer of protein was checked by reversibly staining the filter with Ponceau S, after which the TTFC and V3 loop of HIV. were detected separately by the use of a rabbit TTFC antiserum and a monoclonal antibody specific to the V3 loop of HIV1 type MN. The results show that antigenically authentic TTFC and V3 loop could be detected in the expression strains following induction (FIG. 12a & b respectively).

Use of this procedure has thereby enabled us to demonstrate for the first time that it is possible to express fragments of the HIV1 virus in a food grade organism such as *Lactococcus lactis* suitable for use as an oral vaccine.

Example 4

Production of An Insecticidal Crystal Protein in *L. lactis*

Introduction

Several classes of insecticidal crystal proteins (also known as δ-endotoxins), having different insect host spectra are naturally produced by strains of *Bacillus thuringiensis*. Most of these proteins are prototoxins which form inclusions within the bacteria during sporulation. The crystalline prototoxins are dissolved by the alkaline conditions in the midgut of the insect and are then proteolytically processed to generate smaller active polypeptide toxins. The toxins are proposed to generate pores in the midgut epithelial cells of susceptible insects aid cause them to swell and lyse.[35] Consequently, the insect larvae stop feeding and die.

The specific properties of these toxins has been exploited for over two decades by using different formulations of *Bacillus thuringiensis* to protect crops from damage by insects. The cloning of the genes for crystal protein toxins has provided enormous potential for the improvement of existing approaches. For example, insecticidal crystal proteins have been expressed in transgenic plants[36–38] and plant-associated micro-organisms.[39] The development of a high level and regulated expression system for *L. lactis* has provided an alternative strategy for the low cost production and delivery of insecticidal crystal proteins to crops. The advantage of using *L. lactis* lies with its accepted GRAS (Generally Regarded As Safe) status within industry and established low cost fermentation technology, coupled with the rapidity of toxin formation when this is induced in the *L. lactis* expression system. Whereas toxin formation in wild type isolates of *B. thuringiensis* can require prolonged fermentation times (e.g. 17–24 hours) in order that both spore formation and toxin formation should proceed to completion the biologically active toxin is formed in *L. lactis* within 2 hours after the induction of gene expression. Furthermore, the delivery of the crystal proteins within a robust Gram-positive organism such as *L. lactis* as opposed to a mixture of crystal protein and *Bacillus thuringiensis* spores may improve the stability of the protein in the environment. In order to demonstrate the feasibility of using recombinant *L. lactis* in this way we describe here the cloning and expression of the CrylA(a) crystal protein from *Bacillus thiuringiensis kurstaki* strain HD-1 [40]

1. Construction of a CrylA expression plasmid.

In order to clone the crystal protein gene for CrylA into the T7 expression cassette so that its own initiation codon would be used for translation it was necessary to introduce appropriate restriction sites at the ends of the gene. In order to do this the gene was first assembled in a general cloning vector. Two PCR derived gene fragments of the CrylA gene were sequentially cloned into plasmid pWW as detailed in FIG. 13. The primers were designed to include a Ndel site at the 5' end of the gene which incorporated the ATG (translation initiation) codon and a BamHl site at the 3' end of the gene immediately following the stop codon. The fragments were joined together by a unique Kpnl site present within the gene (FIG. 13). Since the thermostable polymerase used for PCR can introduce mutations into the amplified DNA fragments the major part (95%) of the CrylA gene between the unique Spel and EcoNl sites was deleted from plasmid pWW-PCR CrylA and replaced with the same restriction digest fragment derived from *Bacillus thuringiensis* DNA cloned in plasmid pES1.[41] The resulting plasmid PWW-CrylA was cut with Ndel and BamHl and the 3.5 kb DNA fragment encoding the CrylA fragment cloned between the Ndel and BamHl site in the T7 expression cassette in pUC19NT7 (pUC19NT7 is essentially the same as p18NT7 shown in FIG. 1 except that the T7 cassette and multiple cloning site have been cloned in the opposite orientation; sequence details of the cassette is shown in FIG. 2). Finally the T7 expression cassette incorporating the CrylA gene (Smal-Pstl fragment) was cloned between the SmaI and PstI sites in the *L. lactis/E. coli* shuttle vector pMIG1 to generate the expression plasrnid pLET1-CrylA (FIG. 13). This plasmid was transferred into the expression host strain MG1820, plLPol. The expression strain harbouring pLET1-CrylA was grown and induced as described in Materials and Methods.

2. Expression of CrylA in *L. lactis*.

Figure 14A:
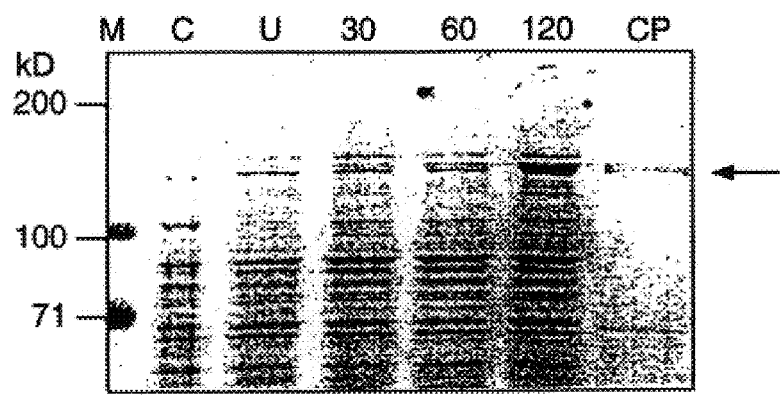
Figure 14B:
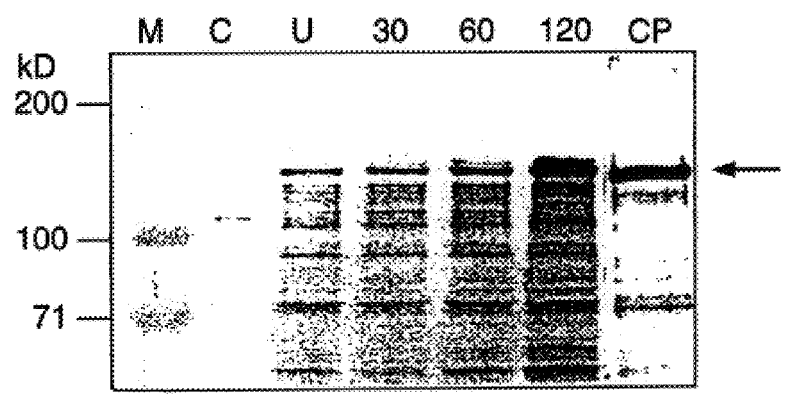
Figure 14C:
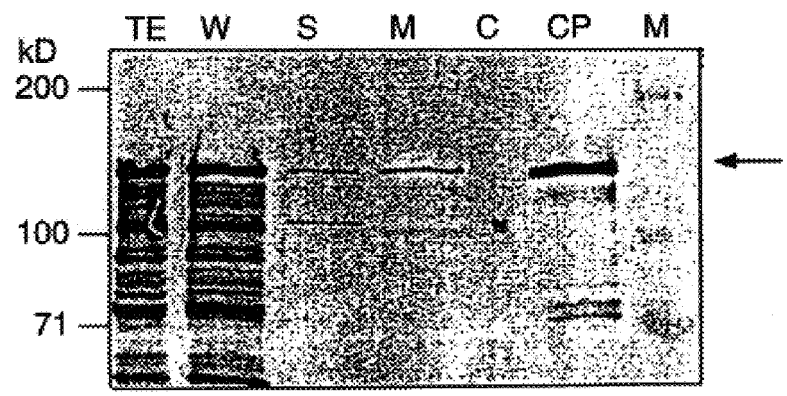

A Coomassie blue stained gel of total cell extracts prepared from the pLET1-CrylA strain following induction showed that a protein of the correct size was clearly visible after two hours (FIG. 14a). The results of Western blotting with polyclonal antisera to the crystal protein confirmed that the CrylA gene product accumulated to high levels within the cell following induction (FIG. 14b). It was also expressed at low levels in uninduced cells. No such protein was detected in total cell extracts prepared from the induced non-expressor control strain. Cells from the pLET1-CrylA expression strain were disrupted two hours after induction by mechanical homogenization as outlined in Materials and Methods. Proportional amounts of the insoluble (wall) membrane (M) and soluble protein fractions were analysed by SDS PAGE and immunoblotting. These results indicated that most of the crystal protein produced in *L. lactis* was insoluble as it is in *Bacillus thuringiensis* (FIG. 14c).

In order to estimate the amounts of CrylA produced in expressing cells the CrylA protein in the insoluble fraction was solubilised by boiling in SDS PAGE sample buffer lacking bromophenol blue. After pelleting the remaining insoluble matter, the supernatant was serially diluted and equal volumes of these dilutions transferred to nitrocellulose filter using a "slot-blot" apparatus. Standard amounts of purified CrylA crystal protein were included as controls. Following immunoblotting the amount of CrylA protein present in the cell extracts was estimated by visual comparison of the bands detected in the sample and standard slots. Based on the total amount of protein recovered from the soluble fraction and from the alkali and SDS treated insoluble fraction we estimate that the CrylA protein accumulated to a level of 30% of total cell protein in induced cells.

3. Biological activity of the induced strain and insoluble cell extracts

In order to determine (on a qualitative basis only) whether either the cells of *L. lactis* in which the CrylA protein had formed, &/or the CrylA protein itself were biologically active toxicity assays were carried out using first instar larvae of the tobacco hornworm (*Manduca sexta*). Approximately $1 \times 10^8$ bacteria of the induced CrylA expresser strain and of a non-expressor control strain were resuspended in 50 μl of medium and applied to the surface of 1 cm blocks of artificial diet. The insoluble cell extracts prepared from approximately $1 \times 10^9$ cells of the expressor and control strains were also applied (in 50 μl) to separate blocks of food. CrylA crystal protein purified from *Bacillus thuringiensis* was used as a positive control. Six larvae were placed in each vial and growth and mortality followed over a four day period. The differences between the vials in which the various forms of the CrylA protein are shown in the following table:

| VIAL NO. | CONTENTS OF VIAL | CONDITION OF LARVAE AT 3 DAYS |
|---|---|---|
| 1 | Insoluble cell Fraction: pLET1-CrylA *L. lactis* expression strain | 3 dead; 3 ungrown |
| 2 | Insoluble cell Fraction; non-expressor strain of *L. lactis* (MG1363) | 6 well grown, healthy active larvae |
| 3 | $1 \times 10^8$ expressor bacteria | 4 dead; 2 ungrown |
| 4 | $1 \times 10^8$ non-expressor bacteria | 6 well grown, healthy, active larvae |
| 5 | Positive control: alkaline extract of CrylA from *B. thuringiensis* | 4 dead; 2 ungrown |

These results conclusively demonstrate that *L. lactis* expressing CrylA as well as the luble extracts from these bacteria were toxic to the larvae of tobacco hornworm.

1. Bojovic, B., G. Djordjevic, and L. Topisirovic. 1991. Improved vector for promoter screening in lactococci. Appl. Environ. Microbiol. 57:385–388.

2. Sibakov, M., T. Koivula, A. von Wright, and I. Palva. 1991. Secretion of TEM B-lactamase with signal sequences isolated from the chromosome of *Lactococcus lactis* subsp. lactis. Appl. Environ. Microbiol. 57:341–348.

3. van de Guchte, M., J. M. B. M. van der Vossen, J. Kok, and G. Venema. 1989. Construction of a lactococcal Expression vector: expression of hen egg white lysozyme in *Lactococcus lactis* subsp. lactis. Appl. Environ. Microbiol 55:224–228.

4. van de Guchte, M., J. Kodde, J. M. B. M. van der Vossen, J. Kok, and G. Venema. 1990. Heterologous gene expression in *Lactococcus lactis* subsp. lactis: synthesis, secretion and processing of the *Bacillus subtilis* neutral protease. Appl. Environ. Microbiol 56:2606–2611.

5. Pillidge, C. J., and L. E. Pearce. 1991. Expression of a B-galactosidase gene from *Clostridium acetobutylicum* in *Lactococcus lactis* subsp. lactis. J. Appl. Bacteriol. 71:78–85.

6. Simons A. F. M., and W. M. de Vos. 1988 DNA fragments, containing a lactic acid bacterium-specific regulator region for the expression of genes for normally heterologous proteins. European Patent Application No.88201203.2

7. Iwaki, M., N. Okahashi, I. Takahashi, T. Kanamoto, Y. Sugita-Konishi, K. Aibara and T. Koga. 1990. Oral immunization with recombinant *Streptococcus lactis* carrying the *Streptococcus mutans* surface protein antigen gene. Infect. Immunity 58:2929–2934.

8. Studier, F. W., A. H. Rosenberg, J. J. Dunn, and J. W. Dubendorf. 1990. Use of a RNA polymerase to direct expression of cloned genes. Methods In Enzymology 185:60–89.

9. de Vos, W. M. 1987. Gene cloning and expression in lactic streptococci. FEMS Microbiol. Reviews 46:281–295.

10. Hager, P. W., and J. C. Rabinowitz. 1985. Translational specificity in *Bacillus subtilis*, p1–29. In D. A Dubnau (ed.), The Molecular Biology of the Bacilli, vol II. Academic Press, Inc., N.Y.

11. Kilpper-B_Iz, R., G. Fischer, and K. Schleifer. 1982. Nucleic acid hybridization of group N and group D streptococci. Curr. Microbiol 7:245–250.

12. de Vos, W. M., and Gasson M. J. 1989. Structure and expression of the *Lactococcus lactis* gene for phospho-b-galactosidase (lacG) in, *Escherichia coli* and *L. lactis*. J.Gen Microbiol. 135:1833–1846.

13. Feitelson, Payne & Kim, *Bacillus Thuringiensis: Insects and Beyond*; Biotechnology, 10: 271–275 (1992).

14. Gasson, M. J. 1983. J. Bacteriol. 154:1–9.

15. Maeda, S., and M. J. Gasson. 1986. J. Gen Microbiol. 132:331–340.

16. Stratagene Ltd., Cambridge UK.

17. Hanahan, D. 1983. J. Mol. Biol. 166:1–19.

18. Danvaloo, P., A. H. Rosenberg, J. J. Dunn, and F. W. Studier. 1984. Cloning and expression of the gene for bacteriophage T7 polymerase. Proc. Natl. Acad. Sci. USA 81:2035–2039.

19. Simon, D., and A. Chopin. 1988. Construction of a vector plasmid family and its use for molecular cloning in Streptococcus lactis. Biochimie 70:559–566.

20. Halpern, J. L., W. H. Habig, E. A. Neale and S. Stibitz. 1990. Cloning and expression of functional fragment C of tetanus toxin. Infect. Immunity 58:1004–1009.

21. Heilig J. S., K. Lech and R. Brent. Triton Lysis. Section 1.7.4. In. Ausubel F. M. et al. (eds) Current Protocols in Molecular Biology. Wiley Interscience, New York.

22. Birnboim, H. C., and Doly, J. 1979 Nucleic Acids Res 7:1513–1519.

23. Maniatis, T., E. F. Fritsch, and J. Sambrook. 1982. Molecular Cloning: A Laboratory Manual. Cold Spring Harbor Laboratory, Cold Spring Harbor, N.Y.

24. Eckert, A. K., and T. A. Kunkel. 1990 . High fidelity DNA synthesis by the Thermus aquaticus DNA polymerase. Nucleic Acids Res. 18:3739–3744.

25. Kiwaki, M., H. Ikemura, M. Shimizu-Kadota and A. Hirashima. 1989. Molecular characterisation of a cell wall-associated proteinase gene from Streptococcus lactis NCDO 763. Mol. Microbiol. 3: 359–369.

26. Dower, W. J., J. F. Miller, and Ragsdale, C. W. 1988. Nucleic Acids Res. 16:6127.

27. Laemmli, U. K. 1970. Cleavage of structural proteins during the assembly of the head of bacteriophage T4. Nature 227:680–685.

28. Burnette, W. H. 1981. Western blotting: electrophoretic transfer of proteins from SDS polyacrylamide gels to unmodified nitrocellulose and radiographic detection with antibody and radioiodinated protein A. Anal. Biochern. 112:195–203.

29. Asseldonk, M. van., G. Rutten, M. Oteman, R. J. Siezen, W. M. de Vos, and G Simons. 1990. Cloning of usp45, a gene encoding a secreted protein from Lactococcus lactis subsp. lactis MG1363. Gene 95:155–160.

30. Gasson, M. J., and P. H. Anderson. 1985. High copy number plasmid vectors for use in lactic streptococci. FEMS Microbiol Letters 30:193–196.

31. Van Rooijen, R. J., and W. M. de Vos. 1990 Molecular cloning, transcriptional analysis, and nucleotide sequence of lacR, a gene encoding the repressor of the lactose phophotransferase system of Lactococcus lactis. J. Biol Chem. 265:18499–18503.

32. Van Rooijen, R. J., S van Schalkwijk, and W. M. de Vos. 1991. Molecular cloning, characterization, and nucleotide sequence of the tagatose 6-phosphate pathway gene cluster of the lactose operon of Lactococcus lactis . J. Biol Chem. 266:7176–7181.

33. Kok, J. (1991) In Genetics and Molecular Biology of Streptococci, Lactococci, and Enterococci. Dunny, G. M., Cleary, P. P., & McKay L. L. (eds) American Society for Microbiology.

34. Kiwaki, M., H. Ikemura, M. Shimizu-Kadota and A., Hirashima. 1989. Molecular characterization of a cell wall-associated proteinase gene from Streptococcus lactis NCDO763. Mol. Microbiol. 3:359–369.

35. Knowles, B. H., and D. J. Ellar, 1987 Colloid-osmotic lysis is a general feature of the mechanism of action of Bacillus thuringiensis d-endotoxin with different insect specificities Biochim. Biophys. Acta. 924, 509–518

36. Barton K. A., H. R. Whiteley, and N.-S. Yang. 1987. Bacillus thuringiensis d-endotoxin expressed in transgenic Nicotiana tabacum provides resistance tolepidopteran insects. Plant Physiol., 85.:1103–1109.

37. Fischoff et al., 1987. Insect tolerant transgenic tomatoe plants. Bio/Tech., 5:807–813

38. Vaeck et al., 1987. Transgenic plants protected from insect attack. Nature, 328:33–37.

39. Obukowicz et al., 1986. Integration of the delta endotoxin gene gene of Bacillus thuringiensis into the chromosome of root colonizing strains of psuedomonads using Tn5. Gene 45;327–331

40. Schnepf, E. H., H. C. Wong, and H. R. Whiteley 1985. the amino acid sequence of a crystal protein from Bacillus thuringiensis deduced from the DNA base sequence. J. Biol. Chem. 260: 6264–6272.

41. Schnepf, E., and H. R. Whiteley. 1981. Delineation of a toxin-encoding segment of a Bacillus thuringiensis crystal protein gene. PNAS 78: 2893–2897.

---

What is claimed is:

1. *Lactococcus lactis* host organism transformed with recombinant DNA comprising:
   a T7 RNA polymerase gene placed under the control of the lac inducible promoter and the lacR gene, and
   a promoter specific for the T7 RNA polymerase upstream of a coding sequence for a desired polypeptide, whereby the promoter specific for said T7 RNA polymerase directs transcription of said coding sequence selectively as a result of expression of said polymerase.

2. *Lactococcus lactis* host organism transformed with recombinant DNA comprising:
   a T7 RNA polymerase gene placed under the control of the lac inducible promoter and the lacr gene;
   a promoter specific for the T7 RNA polymerase upstream of a coding sequence for a desired polypeptide, whereby the promoter specific for said T7 RNA polymerase directs transcription of said coding sequence selectively as a result of expression of said polymerase; and,
   a secretory signal sequence, derived from a protein endogenous to *Lactococcus lactis* operatively linked to said coding sequence for the desired polypeptide, whereby the desired polypeptide is secreted from said host organism.

* * * * *

UNITED STATES PATENT AND TRADEMARK OFFICE
CERTIFICATE OF CORRECTION

PATENT NO.    : 6,221,648 B1
DATED         : April 24, 2001
INVENTOR(S)   : Richard Williams Falla Le Page and Jeremy Mark Wells It is certified that error appears in the above-identified patent and that said Letters Patent is hereby corrected as shown below:

The correct spelling of the assignee's name is: Microbial Technics Ltd.

Signed and Sealed this

Twenty-sixth Day of February, 2002

Attest:

Attesting Officer

JAMES E. ROGAN
*Director of the United States Patent and Trademark Office*

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 89 base pairs
      (B) TYPE: nucleic acid
      (C) STRANDEDNESS: double
      (D) TOPOLOGY: circular (xi) SEQUENCE DESCRIPTION: SEQ ID NO:1:

```
TAATACGACT CACTATAGGG AGACCACAAC GGTTTCCCTC TAGAAATAAT TTTGTTTAAC        60
```

```
TTTAAGAAGG AGATATACAT ATGGCTAGC                                              89

(2) INFORMATION FOR SEQ ID NO:2:

(i) SEQUENCE CHARACTERISTICS:
        (A) LENGTH: 15 base pairs
        (B) TYPE: nucleic acid
        (C) STRANDEDNESS: double
        (D) TOPOLOGY: circular (ix) FEATURE:
        (A) NAME/KEY: CDS
        (B) LOCATION: 1..15

(xi) SEQUENCE DESCRIPTION: SEQ ID NO:2:

ATG GGT CGC GGA TCC                                                          15
Met Gly Arg Gly Ser
 1               5

(2) INFORMATION FOR SEQ ID NO:3:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:3:

Met Gly Arg Gly Ser
 1               5

(2) INFORMATION FOR SEQ ID NO:4:

(i) SEQUENCE CHARACTERISTICS:
        (A) LENGTH: 45 base pairs
        (B) TYPE: nucleic acid
        (C) STRANDEDNESS: double
        (D) TOPOLOGY: circular (xi) SEQUENCE DESCRIPTION: SEQ ID NO:4:

GCATAACCCC TTGGGGCCTC TAAACGGGTC TTGAGGGGTT TTTTG                             45

(2) INFORMATION FOR SEQ ID NO:5:

(i) SEQUENCE CHARACTERISTICS:
        (A) LENGTH: 51 base pairs
        (B) TYPE: nucleic acid
        (C) STRANDEDNESS: double
        (D) TOPOLOGY: circular (xi) SEQUENCE DESCRIPTION: SEQ ID NO:5:

TCTAGAAATA ATTTTGTTTA ACTTTAAGAA GGAGATATAC ATATGAAAAA A                      51

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: double
        (D) TOPOLOGY: circular (ix) FEATURE:
        (A) NAME/KEY: CDS
        (B) LOCATION: 1..15

(xi) SEQUENCE DESCRIPTION: SEQ ID NO:6:

GTT TAC GCT GTC GAC GGATCC                                                   21
```

```
Val Tyr Ala Val Asp
            10

(2) INFORMATION FOR SEQ ID NO:7:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:7:

Val Tyr Ala Val Asp
 1           5

(2) INFORMATION FOR SEQ ID NO:8:

(i) SEQUENCE CHARACTERISTICS:
        (A) LENGTH: 52 base pairs
        (B) TYPE: nucleic acid
        (C) STRANDEDNESS: double
        (D) TOPOLOGY: circular (xi) SEQUENCE DESCRIPTION: SEQ ID NO:8:

TCTAGAGCTT CATATGAAAC TTTTGGAAAG TGGAGGATAT TGGATGCAAA GG            52

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: double
        (D) TOPOLOGY: circular (ix) FEATURE:
        (A) NAME/KEY: CDS
        (B) LOCATION: 1..15

(xi) SEQUENCE DESCRIPTION: SEQ ID NO:9:

AAG GCG GCG GTC GAC GGATCC                                          21
Lys Ala Ala Val Asp
            10

(2) INFORMATION FOR SEQ ID NO:10:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:10:

Lys Ala Ala Val Asp
 1           5

(2) INFORMATION FOR SEQ ID NO:11:

(i) SEQUENCE CHARACTERISTICS:
        (A) LENGTH: 39 amino acids
        (B) TYPE: amino acid
        (D) TOPOLOGY: linear (ii) MOLECULE TYPE: protein (xi) SEQUENCE DESCRIPTION: SEQ ID NO:11:

Asn Cys Thr Arg Pro Asn Tyr Asn Lys Arg Lys Arg Ile His Ile Gly
 1               5                  10                  15
```

Pro Gly Arg Ala Phe Tyr Thr Thr Lys Asn Ile Ile Gly Thr Ile Arg
            20                  25                  30

Gln Ala His Cys Asn Ile Ser
        35

(2) INFORMATION FOR SEQ ID NO:12:

(i) SEQUENCE CHARACTERISTICS:
        (A) LENGTH: 86 amino acids
        (B) TYPE: amino acid
        (D) TOPOLOGY: linear (ii) MOLECULE TYPE: protein (xi) SEQUENCE DESCRIPTION: SEQ ID NO:12:

Arg Ser Leu Leu Leu Asn Gly Ser Leu Ala Glu Glu Val Val Ile
1               5                   10                  15

Arg Ser Glu Asn Phe Thr Asp Asn Ala Lys Thr Ile Ile Val His Leu
            20                  25                  30

Asn Glu Ser Val Gln Ile Asn Cys Thr Arg Pro Asn Tyr Asn Lys Arg
        35                  40                  45

Lys Arg Ile His Ile Gly Pro Gly Arg Ala Phe Tyr Thr Thr Lys Asn
    50                  55                  60

Ile Ile Gly Thr Ile Arg Gln Ala His Cys Asn Ile Ser Arg Ala Lys
65                  70                  75                  80

Trp Asn Asp Thr Gly Ser
                85

(2) INFORMATION FOR SEQ ID NO:13:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:13:

GATCGGCCAA GCTTCATATG AAACTTTTGG AAAGTGGAGG ATATTGGA         48

(2) INFORMATION FOR SEQ ID NO:14:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:14:

CCGACGGATC CGTCGACCGC CGCCTTTGCT TGGATTTCGC CGACTGGC         48

(2) INFORMATION FOR SEQ ID NO:15:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:15:

CGGGATCCCG ACAAACCATA CATTAGAA                               28

(2) INFORMATION FOR SEQ ID NO:16:

-continued

```
    (i) SEQUENCE CHARACTERISTICS:
         (A) LENGTH: 28 base pairs
         (B) TYPE: nucleic acid
         (C) STRANDEDNESS: single
         (D) TOPOLOGY: linear (xi) SEQUENCE DESCRIPTION: SEQ ID NO:16:

CGGGATCCGA AATGCTACGT AGAAGTAC                                            28
```